United States Patent
Genet et al.

(10) Patent No.: US 6,383,230 B1
(45) Date of Patent: May 7, 2002

(54) CATIONIC MONOBENZENIC DYES, THEIR USE FOR THE OXIDATION-DYEING OF KERATIN FIBERS, DYE COMPOSITIONS AND DYEING PROCESSES

(75) Inventors: Alain Genet, Aulnay sous Bois; Alan Lagrange, Coupvray, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/484,994

(22) Filed: Jan. 18, 2000

(30) Foreign Application Priority Data

Jan. 19, 1999 (FR) .............................. 99 00504

(51) Int. Cl.⁷ ................................. A61K 7/13
(52) U.S. Cl. ...................... 8/405; 8/405; 8/406; 8/408; 8/409; 8/410; 8/412; 540/1; 544/3; 546/1; 548/125; 549/13
(58) Field of Search ...................... 8/405, 406, 408, 8/409, 410, 412; 549/13; 548/125; 546/1; 544/3; 540/1

(56) References Cited

U.S. PATENT DOCUMENTS

| | | | |
|---|---|---|---|
| 4,823,985 A | 4/1989 | Grollier et al. | 222/1 |
| 4,888,025 A | 12/1989 | Bugaut et al. | 8/405 |
| 5,139,532 A * | 8/1992 | Chan et al. | 8/405 |
| 6,241,784 B1 * | 1/2001 | De La Mettrie et al. | 8/406 |

FOREIGN PATENT DOCUMENTS

| | | |
|---|---|---|
| DE | 23 59 399 | 6/1975 |
| DE | 38 43 892 | 6/1990 |
| DE | 41 33 957 | 4/1993 |
| DE | 195 43 988 | 5/1997 |
| FR | 2 520 358 | 7/1983 |
| FR | 2 586 913 | 3/1987 |
| FR | 2 630 438 | 10/1989 |
| FR | 2 733 749 | 11/1996 |
| FR | 2 766 178 | 1/1999 |
| GB | 1 026 978 | 3/1962 |
| GB | 1 153 196 | 7/1965 |
| JP | 63-169571 | 7/1988 |
| JP | 9-110659 | 4/1997 |
| WO | WO 94/08969 | 4/1994 |
| WO | WO 94/08970 | 4/1994 |
| WO | WO 96/15765 | 5/1996 |

OTHER PUBLICATIONS

Teiji Kimura et al. (Structure–Activity Relationship of N–(2–(Dimethylamino)–6–(3–(5–methyl–4–phenyl–1H–imidazol–1–yl)propox)phenyl)–N'–pentylurea and analoges.). J.Med. Chem. 1993, 36, 1630–1640.*
English language Derwent Abstract of DE 23 59 399, No date.
English language Derwent Abstract of DE 38 43 892, Jun. 1990.
English language Derwent Abstract of DE 41 33 957, Apr. 1993.
English language Derwent Abstract of DE 195 43 988, May 1997.
English language Derwent Abstract of FR 2 630 438, Oct. 1989.
English language Derwent Abstract of FR 2 733 749, Nov. 1996.
English language Derwent Abstract of FR 2 766 178, Jan. 1999.
English language Derwent Abstract of JP 63–169571, Jul. 1988.
English language Derwent Abstract of JP 9–110659, Apr. 1997.

* cited by examiner

Primary Examiner—Yogendra N. Gupta
Assistant Examiner—Eisa Elhilo
(74) Attorney, Agent, or Firm—Finnegan, Henderson, Farabow, Garrett & Dunner, L.L.P.

(57) ABSTRACT

The invention relates to novel monobenzenic dyes including at least one cationic group Z, Z chosen from quaternized aliphatic chains, aliphatic chains including at least one quaternized saturated ring and aliphatic chains including at least one quaternized unsaturated ring, to their use as oxidation-dye precursors for the oxidation-dyeing of keratin fibers, to dye compositions containing them and to oxidation-dyeing processes using them.

36 Claims, No Drawings

CATIONIC MONOBENZENIC DYES, THEIR USE FOR THE OXIDATION-DYEING OF KERATIN FIBERS, DYE COMPOSITIONS AND DYEING PROCESSES

The invention relates to novel monobenzenic dyes comprising at least one cationic group Z, Z chosen from quaternized aliphatic chains, aliphatic chains comprising at least one quaternized saturated ring and aliphatic chains comprising at least one quaternized unsaturated ring, to their use as oxidation-dye precursors for the oxidation-dyeing of keratin fibers, to dye compositions containing them and to oxidation-dyeing processes using them.

It is a known practice to dye keratin fibers, in particular human hair, with dye compositions comprising oxidation-dye precursors, in particular para-phenylenediamines, ortho-aminophenols or para-aminophenols and heterocyclic compounds such as diaminopyrazole derivatives, which are generally referred to as oxidation bases. The oxidation-dye precursors, or oxidation bases, are colorless or weakly coloured compounds which, when combined with oxidizing products, can give rise to coloured compounds and dyes by a process of oxidative condensation.

It is also known that the shades obtained with these oxidation bases can be varied by combining them with couplers or coloration modifiers, the latter being chosen in particular from aromatic meta-diamines, meta-aminophenols, meta-diphenols and certain heterocyclic compounds such as, for example, indole couplers.

The variety of molecules used as oxidation bases and couplers makes it possible to obtain a wide range of colors. The so-called "permanent" coloration obtained by means of these oxidation dyes must, moreover, satisfy a certain number of requirements. Specifically, the oxidation dyes must have no toxicological drawbacks, must allow shades of the desired strength to be obtained, and have good resistance to external agents (light, bad weather, washing, permanent-waving, perspiration and friction).

The dyes must also allow white hairs to be covered. Lastly, they must be as unselective as possible, i.e., they must allow the smallest possible differences in coloration to be produced over the entire length of the same keratin fiber, which may indeed be differently sensitized (i.e., damaged) between its tip and its root.

The inventors have discovered, entirely surprisingly and unexpectedly, that novel cationic monobenzenic dyes of formula (I) defined below, comprising at least one cationic group Z, Z chosen from quaternized aliphatic chains, aliphatic chains comprising at least one quaternized saturated ring and aliphatic chains comprising at least one quaternized unsaturated ring, are not only suitable for use as oxidation-dye precursors, but also allow dye compositions to be obtained which lead to strong colorations, in a wide range of shades, and which have excellent properties of resistance to the various treatments to which keratin fibers may be subjected.

These discoveries form the basis of the present invention.

A first subject of the invention is thus novel compounds of formula (I) below, and the acid addition salts thereof:

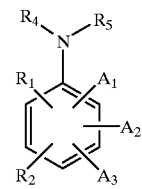

(I)

in which:

$A_1$, $A_2$ and $A_3$, which may be identical or different, are chosen from a group —$NR_7R_8$ and a hydroxyl radical; one and only one of the groups $A_1$, $A_2$ and $A_3$ can also represent a group $R_3$ as defined below;

$R_1$, $R_2$ and $R_3$, which may be identical or different, are chosen from a hydrogen atom; a halogen atom; a group Z as defined below; a ($C_1$–$C_6$)alkylcarbonyl radical; an amino($C_1$–$C_6$) alkylcarbonyl radical; an N-Z-amino($C_1$–$C_6$) alkylcarbonyl radical; an N-($C_1$–$C_6$)alkylamino ($C_1$–$C_6$)alkylcarbonyl radical; an N,N-di($C_1$–$C_6$) alkylamino ($C_1$–$C_6$)alkylcarbonyl radical; an amino ($C_1$–$C_6$)alkylcarbonyl($C_1$–$C_6$)alkyl radical; an N-Z-amino($C_1$–$C_6$)alkylcarbonyl($C_1$–$C_6$)alkyl radical; an N-($C_1$–$C_6$)alkylamino($C_1$–$C_6$)alkylcarbonyl($C_1$–$C_6$) alkyl radical; an N,N-di($C_1$–$C_6$) alkylamino($C_1$–$C_6$) alkylcarbonyl($C_1$–$C_6$)alkyl radical; a carboxyl radical; a ($C_1$–$C_6$)alkylcarboxyl radical; a ($C_1$–$C_6$) alkylsulphonyl radical; an aminosulphonyl radical; an N-Z-aminosulphonyl radical; a ($C_1$–$C_6$)N-alkylaminosulphonyl radical; an N,N-di($C_1$–$C_6$)alkylaminosulphonyl radical; a ($C_1$–$C_6$) aminosulphonylalkyl radical; a ($C_1$–$C_6$)N-Z-aminosulphonylalkyl radical; an N-($C_1$–$C_6$)alkylaminosulphonyl($C_1$–$C_6$)alkyl radical; an N,N-di($C_1$–$C_6$)alkylaminosulphonyl($C_1$–$C_6$)alkyl radical; a carbamyl radical; an N-($C_1$–$C_6$)alkylcarbamyl radical; an N,N-di($C_1$–$C_6$) alkylcarbamyl radical; a carbamyl($C_1$–$C_6$)alkyl radical; an N-($C_1$–$C_6$) alkylcarbamyl($C_1$–$C_6$)alkyl radical;

an N,N-di($C_1$–$C_6$)alkylcarbamyl($C_1$–$C_6$)alkyl radical; a ($C_1$–$C_6$)alkyl radical; a ($C_1$–$C_6$)monohydroxyalkyl radical; a ($C_2$–$C_6$) polyhydroxyalkyl radical; a ($C_1$–$C_6$)alkoxy($C_1$–$C_6$) alkyl radical; a ($C_1$–$C_6$)trifluoroalkyl radical; a cyano radical; a group $OR_6$ or $SR_6$; an amino group protected by a ($C_1$–$C_6$)alkylcarbonyl, ($C_1$–$C_6$)alkylcarboxyl, trifluoro($C_1$–$C_6$)alkylcarbonyl, amino($C_1$–$C_6$) alkylcarbonyl, N-Z-amino($C_1$–$C_6$)alkylcarbonyl, N-($C_1$–$C_6$)alkylamino($C_1$–$C_6$)alkylcarbonyl, N,N-di ($C_1$–$C_6$)alkylamino($C_1$–$C_6$)alkylcarbonyl, ($C_1$–$C_6$) alkylcarboxyl, carbamyl, N-($C_1$–$C_6$)alkylcarbamyl, N,N-di($C_1$–$C_6$)alkylcarbamyl, $C_1$–$C_6$ alkylsulphonyl, aminosulphonyl, N-Z-aminosulphonyl, ($C_1$–$C_6$)N-alkylaminosulphonyl, N,N-di($C_1$–$C_6$) alkylaminosulphonyl, thiocarbamyl or formyl radical, or with the group Z defined below in which a linker arm D comprises a ketone function directly attached to the nitrogen atom of the amino group; a ($C_1$–$C_6$)aminoalkyl radical in which the alkyl is unsubstituted or substituted with one or more hydroxyl radicals; a ($C_1$–$C_6$)aminoalkyl radical in which the alkyl is unsubstituted or substituted with one or more hydroxyl radicals and in which the amine is substituted with one or two radicals, which may be identical or different, chosen from alkyl, ($C_1$–$C_6$)monohydroxyalkyl, ($C_2$–$C_6$)polyhydroxyalkyl, ($C_1$–$C_6$)alkylcarbonyl, carbamyl, N-($C_1$–$C_6$)alkylcarbamyl, N,N-di($C_1$–$C_6$)alkylcarbamyl, ($C_1$–$C_6$)alkylsulphonyl, formyl, trifluoro($C_1$–$C_6$)alkylcarbonyl, ($C_1$–$C_6$)alkylcarboxyl and thiocarbamyl radicals, or from a group Z as defined below, or which may form, together with the nitrogen atom to which they are attached, a carbonaceous 5- or 6-membered ring or which contains one or more hetero atoms;

$R_6$ is chosen from a ($C_1$–$C_6$)alkyl radical; a ($C_1$–$C_6$)monohydroxyalkyl radical; a ($C_2$–$C_6$)polyhydroxyalkyl radical; a group Z as defined below; a ($C_1$–$C_6$)alkoxy($C_1$–$C_6$)alkyl radical; an aryl radical; a benzyl radical; a carboxy($C_1$–$C_6$)alkyl radical; a ($C_1$–$C_6$)alkylcarboxy($C_1$–$C_6$)alkyl radical; a cyano($C_1$–$C_6$)alkyl radical; a carbamyl($C_1$–$C_6$)alkyl radical; an N-($C_1$–$C_6$)alkyl carbamyl($C_1$–$C_6$)alkyl radical; an N,N-di($C_1$–$C_6$)alkylcarbamyl ($C_1$–$C_6$)alkyl radical; a ($C_1$–$C_6$)trifluoroalkyl radical; a ($C_1$–$C_6$)aminosulphonylalkyl radical; a ($C_1$–$C_6$)N-Z-aminosulphonylalkyl radical; an N-($C_1$–$C_6$)alkylamino-sulphonyl($C_1$–$C_6$)alkyl radical; an N,N-di($C_1$–$C_6$)alkylaminosulphonyl-($C_1$–$C_6$)alkyl radical; a ($C_1$–$C_6$)alkylsulphinyl ($C_1$–$C_6$)alkyl radical; a ($C_1$–$C_6$)alkylsulphonyl ($C_1$–$C_6$)alkyl radical; a ($C_1$–$C_6$)alkylcarbonyl ($C_1$–$C_6$)alkyl radical; a ($C_1$–$C_6$)aminoalkyl radical in which the alkyl is unsubstituted or substituted with one or more hydroxyl radicals; a ($C_1$–$C_6$)aminoalkyl radical in which the alkyl is unsubstituted or substituted with one or more hydroxyl radicals and in which the amine is substituted with one or two identical or different radicals chosen from ($C_1$–$C_6$)alkyl, ($C_1$–$C_6$)monohydroxyalkyl, ($C_2$–$C_6$)polyhydroxyalkyl, ($C_1$–$C_6$)alkylcarbonyl, formyl, trifluoro-($C_1$–$C_6$)alkylcarbonyl, ($C_1$–$C_6$)alkylcarboxyl, carbamyl, N-($C_1$–$C_6$)alkylcarbamyl, N,N-di-($C_1$–$C_6$)alkylcarbamyl, thiocarbamyl and ($C_1$–$C_6$) alkylsulphonyl radicals, or from a group Z as defined below; or which may form, together with the nitrogen atom to which they are attached, a carbonaceous 5- or 6-membered ring or which contains one or more hetero atoms;

$R_4$, $R_5$, $R_7$ and $R_8$, which may be identical or different, are chosen from a hydrogen atom; a group Z as defined below, in which the linker arm D contains no ketone functions directly linked to the nitrogen atom carrying the $R_4$ and $R_5$ radicals; a ($C_1$–$C_6$)alkyl radical; a ($C_1$–$C_6$) monohydroxyalkyl radical;

a ($C_2$–$C_6$)polyhydroxyalkyl radical; a ($C_1$–$C_6$)alkoxy($C_1$–$C_6$)alkyl radical; an aryl radical; a benzyl radical; a cyano($C_1$–$C_6$)alkyl radical; a carbamyl($C_1$–$C_6$)alkyl radical; an N-($C_1$–$C_6$)alkylcarbamyl($C_1$–$C_6$)alkyl radical; an N,N-di($C_1$–$C_6$)alkylcarbamyl($C_1$–$C_6$)alkyl radical; a thiocarbamyl($C_1$–$C_6$)alkyl radical; a ($C_1$–$C_6$)trifluoroalkyl radical; a ($C_1$–$C_6$)sulphoalkyl radical; a ($C_1$–$C_6$)alkylcarboxy($C_1$–$C_6$)alkyl radical; a ($C_1$–$C_6$)alkylsulphinyl($C_1$–$C_6$)alkyl radical; a ($C_1$–$C_6$)aminosulphonylalkyl radical; a ($C_1$–$C_6$)N-Z-aminosulphonylalkyl radical; an N-($C_1$–$C_6$)alkylaminosulphonyl($C_1$–$C_6$)alkyl radical; an N,N-di($C_1$–$C_6$)alkylaminosulphonyl($C_1$–$C_6$)alkyl radical; a ($C_1$–$C_6$)alkylcarbonyl($C_1$–$C_6$)alkyl radical; a ($C_1$–$C_6$)aminoalkyl radical in which the alkyl is unsubstituted or substituted with one or more hydroxyl radicals; a ($C_1$–$C_6$)aminoalkyl radical in which the alkyl is unsubstituted or substituted with one or more hydroxyl radicals and in which the amine is substituted with one or two identical or different radicals chosen from ($C_1$–$C_6$)alkyl, ($C_1$–$C_6$)monohydroxyalkyl, ($C_2$–$C_6$)polyhydroxyalkyl, ($C_1$–$C_6$)alkylcarbonyl, carbamyl, N-($C_1$–$C_6$)alkylcarbamyl, N,N-di($C_1$–$C_6$)alkylcarbamyl, ($C_1$–$C_6$)alkylsulphonyl, formyl, trifluoro($C_1$–$C_6$)alkylcarbonyl, ($C_1$–$C_6$)alkylcarboxyl and thiocarbamyl radicals, or from a group Z as defined below; or which may form, together with the nitrogen atom to which they are attached, a carbonaceous 5- or 6-membered ring or which contains one or more hetero atoms;

Z is chosen from the unsaturated cationic groups of formulae (II) and (III) below, and the saturated cationic groups of formula (IV) below:

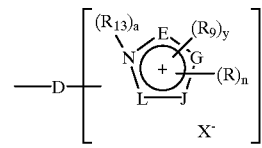

(II)

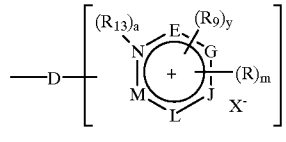

(III)

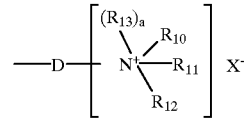

(IV)

in which:
D is a linker arm which represents a linear or branched alkyl chain preferably comprising from 1 to 14 carbon atoms, which can be interrupted by one or more hetero atoms such as oxygen, sulphur or nitrogen atoms, and which can be substituted with one or more hydroxyl or ($C_1$–$C_6$)alkoxy radicals, and which can bear one or more ketone functional groups;

the ring members E, G, J, L and M, which may be identical or different, are chosen from a carbon, oxygen, sulphur or nitrogen atom;

n is an integer ranging from 0 to 4;

m is an integer ranging from 0 to 5;

the R radicals, which may be identical or different, are chosen from a second group Z identical to or different from the first group Z; a halogen atom; a hydroxyl radical; a ($C_1$–$C_6$)alkyl radical; a ($C_1$–$C_6$)monohydroxyalkyl radical; a ($C_2$–$C_6$)polyhydroxyalkyl radical; a nitro radical; a cyano radical; a cyano($C_1$–$C_6$)alkyl radical; a $C_1$–$C_6$ alkoxy radical; a tri($C_1$–$C_6$)alkylsilane($C_1$–$C_6$)alkyl radical; an amido radical; an aldehydo radical; a carboxyl radical; a ($C_1$–$C_6$) alkylcarbonyl radical; a thio radical; a ($C_1$–$C_6$)thioalkyl radical; a ($C_1$–$C_6$)alkylthio radical; an amino radical; an amino radical protected with a ($C_1$–$C_6$)alkylcarbonyl; carbamyl or ($C_1$–$C_6$)alkylsulphonyl radical; or an NHRO or NROR" group in which RO and R", which may be identical or different, are chosen from a ($C_1$–$C_6$)alkyl radical, a ($C_1$–$C_6$)monohydroxyalkyl radical or a ($C_2$–$C_6$) polyhydroxyalkyl radical;

$R_9$ is chosen from a ($C_1$–$C_6$)alkyl radical; a ($C_1$–$C_6$) monohydroxyalkyl radical; a ($C_2$–$C_6$)polyhydroxyalkyl radical; a cyano($C_1$–$C_6$)alkyl radical; a tri($C_1$–$C_6$)alkylsilane($C_1$–$C_6$)alkyl radical; a ($C_1$–$C_6$) alkoxy($C_1$–$C_6$)alkyl radical; a carbamyl-($C_1$–$C_6$)alkyl radical; a ($C_1$–$C_6$)alkylcarboxy($C_1$–$C_6$)-alkyl radical; a benzyl radical or a second group Z identical to or different from the first group Z;

$R_{10}$, $R_{11}$ and $R_{12}$, which may be identical or different, are chosen from a ($C_1$–$C_6$)alkyl radical; a ($C_1$–$C_6$) monohydroxyalkyl radical; a ($C_2$–$C_6$)polyhydroxyalkyl radical; a ($C_1$–$C_6$)alkoxy ($C_1$–$C_6$)alkyl radical; a cyano($C_1$–$C_6$)alkyl radical; an aryl radical; a benzyl radical; a ($C_1$–$C_6$)amidoalkyl radical; a tri($C_1$–$C_6$)alkylsilane ($C_1$–$C_6$)alkyl radical or a ($C_1$–$C_6$)aminoalkyl radical in which the amine is protected with a ($C_1$–$C_6$) alkylcarbonyl, carbamyl or $C_1$–$C_6$ alkylsulphonyl radical; two of the radicals $R_{10}$, $R_{11}$ and $R_{12}$ may also form together, with the nitrogen atom to which they are attached, a saturated carbonaceous 5- or 6-membered ring or a saturated 5- or 6-membered ring which contains one or more heteroatoms, such as, for example, a pyrrolidine ring, a piperidine ring, a piperazine ring or a morpholine ring, it being possible for the ring to be unsubstituted or substituted with a halogen atom, a hydroxyl radical, a ($C_1$–$C_6$)alkyl radical, a ($C_1$–$C_6$)monohydroxyalkyl radical, a ($C_2$–$C_6$) polyhydroxyalkyl radical, a nitro radical, a cyano radical, a cyano($C_1$–$C_6$)alkyl radical, a ($C_1$–$C_6$)alkoxy radical, a tri($C_1$–$C_6$)alkylsilane($C_1$–$C_6$)alkyl radical, an amido radical, a formyl radical, a carboxyl radical, a keto($C_1$–$C_6$)alkyl radical, a thio radical, a ($C_1$–$C_6$) thioalkyl radical, a ($C_1$–$C_6$)alkylthio radical, an amino radical or an amino radical protected by a ($C_1$–$C_6$) alkylcarbonyl, carbamyl or ($C_1$–$C_6$)alkylsulphonyl radical;one of the $R_{10}$, $R_{11}$ and $R_{12}$ radicals can also represent a second group Z identical to or different from the first group Z;

$R_{13}$ is chosen from a ($C_1$–$C_6$)alkyl radical; a ($C_1$–$C_6$) monohydroxy-alkyl radical;
a ($C_2$–$C_6$)polyhydroxyalkyl radical; an aryl radical; a benzyl radical; an
amino($C_1$–$C_6$)alkyl radical, an amino($C_1$–$C_6$)alkyl radical, the amine of which is protected by a ($C_1$–$C_6$) alkylcarbonyl, carbamyl or ($C_1$–$C_6$)alkylsulphonyl radical; a carboxy($C_1$–$C_6$)alkyl radical; a cyano ($C_1$–$C_6$)alkyl radical; a
carbamyl($C_1$–$C_6$)alkyl radical; a trifluoro($C_1$–$C_6$)alkyl radical; a
tri($C_1$–$C_6$)alkylsilyl($C_1$–$C_6$)alkyl radical; a sulphonamido ($C_1$–$C_6$)alkyl radical; a
($C_1$–$C_6$)alkylcarboxy($C_1$–$C_6$)alkyl radical; a ($C_1$–$C_6$) alkylsulphinyl($C_1$–$C_6$)alkyl radical; a ($C_1$–$C_6$) alkylsulphonyl($C_1$–$C_6$)alkyl radical; a
($C_1$–$C_6$)alkylketo($C_1$–$C_6$)alkyl radical; an N-($C_1$–$C_6$) alkylcarbamyl($C_1$–$C_6$)alkyl radical; an N-($C_1$–$C_6$) alkylsulphonamido($C_1$–$C_6$)alkyl radical;

a and y are integers equal to 0 or 1; with the following conditions:
in the unsaturated cationic groups of formula (II):
when a=0, the linker arm D is attached to the nitrogen atom,
when a=1, the linker arm D is attached to one of the ring members E, G, J or L,
y can take the value 1 only:
1) when the ring members E, G, J and L simultaneously represent a carbon atom and when the $R_9$ radical is carried by the nitrogen atom of the unsaturated ring; or else
2) when at least one of the ring members E, G, J and L represents a nitrogen atom to which the $R_9$ radical is attached;
in the unsaturated cationic groups of formula (III):
when a=0, the linker arm D is attached to the nitrogen atom,
when a=1, the linker arm D is attached to one of the ring members E, G, J, L or M,
y can take the value 1 only when at least one of the ring members E, G, J, L and M represents a divalent atom and when the $R_9$ radical is carried by the nitrogen atom of the unsaturated ring;
in the cationic groups of formula (IV):
when a=0, then the linker arm D is attached to the nitrogen atom carrying the $R_{10}$ to $R_{12}$ radicals,
when a=1, then two of the $R_{10}$ to $R_{12}$ radicals jointly form, with the nitrogen atom to which they are attached, a saturated 5- or 6-membered ring as defined above, and the linker arm D is carried by a carbon atom of the saturated ring;

$X^-$ is a monovalent or divalent anion and is preferably chosen from a halogen atom, such as chlorine, bromine, fluorine or iodine, a hydroxide, a hydrogen sulphate or a ($C_1$–$C_6$)alkyl sulphate, such as, for example, a methyl sulphate or an ethyl sulphate;

with the overall proviso that the number of Z cationic groups is at least equal to 1.

As mentioned above, the colorations obtained with the oxidation-dye composition containing the dye(s) of formula (I) in accordance with the invention are strong and produce a wide range of colors. They moreover have excellent properties of resistance to the action of various external agents (light, bad weather, washing, permanent-waving, perspiration, friction). These properties are particularly noteworthy with regard to the resistance of the colorations obtained to the action of light, washing, permanent-waving and perspiration.

In formulae (I), (II), (III) and (IV) above, the alkyl and alkoxy radicals can be linear or branched.

Examples of rings of the unsaturated Z groups of formula (II) above may include, but are not limited to, pyrrole, imidazole, pyrazole, oxazole, thiazole and triazole rings.

Examples of the rings of the unsaturated Z groups of formula (III) above may include, but are not limited to, pyridine, pyrimidine, pyrazine, oxazine and triazine rings.

The compounds of formula (I), according to the invention, are preferably chosen from:
1-(2-(2-amino-4-hydroxyphenylamino)ethyl)-3-methyl-3H-imidazol-1-ium chloride;

1-{2-((3-amino-4-methylaminophenyl)methylamino)]
ethyl}-3-methyl-3H-imidazol-1-ium chloride;

1-{2-((3-amino-4-methylaminophenyl)methylamino)
ethyl}-1,4-dimethyl-1-piperazinium chloride;

{2-((3-amino-4-methylaminophenyl)methylamino)
ethyl}-triethylammonium chloride;

1-(2-(2-amino-4-hydroxyphenylamino)ethyl)-1,4-
dimethyl-1-piperazinium chloride;

(2-{2-amino-4-(bis(2-hydroxyethyl)amino)
phenylamino}-ethyl)diethylmethylammonium chloride;

3-(3-{3-(3-methyl-3H-imidazol-1-ium)propylamino)-
4-aminophenylamino}propyl)-1-methyl-3H-imidazol-
1-ium dichloride;

3-methyl-1-(2-(2,4,5-trihydroxyphenylamino)ethyl)-3H-
imidazol-1-ium chloride;

1-(2-(2-amino-5-ethoxy-4-hydroxyphenylamino)ethyl)-
3-methyl-3H-imidazol-1-ium chloride;

1-(2-(2-amino-5-hydroxy-4-methoxyphenylamino)
ethyl)-3-methyl-3H-imidazol-ium chloride;

1-(2-{4-amino-5-(2-(diethylmethylammonium)
ethylamino)-2-hydroxyphenoxy}ethyl)-3-methyl-3H-
imidazol-1-ium dichloride; and acid addition salts
thereof.

The acid addition salts for the compounds of formula (I), in accordance with the invention, are preferably chosen from hydrochlorides, hydrobromides, sulphates, citrates, succinates, tartrates, lactates and acetates.

The compounds of formula (I), in accordance with the invention, can be easily obtained according to methods that are well known in the art, by reduction of the corresponding cationic nitro compounds.

This reduction step (production of a primary aromatic amine), which may or may not be followed by a salification step, is generally, for convenience, the final step of the synthesis.

This reduction can take place earlier in the sequence of reactions leading to the preparation of the compounds of formula (I), and, according to well-known processes, it is then necessary to "protect" the primary amine created (for example by an acetylation, benzenesulphonation, etc. step), then to carry out the desired substitution(s) or modification(s) (including quaternization) and to end by "deprotecting" (generally in acidic medium) the amine function.

Similarly, the phenolic function can be protected according to well-known processes, with a benzyl radical ("deprotection" by catalytic reduction) or with an ram acetyl or mesyl radical ("deprotection" in acidic medium).

When the synthesis is complete, the compounds of formula (I), in accordance with the invention, may, if necessary, be recovered by methods which are well known in the art, such as crystallization or distillation.

Another subject of the invention is the use of the compounds of formula (I), in accordance with the invention, as oxidation-dye precursors for the oxidation-dyeing of keratin fibers, and in particular of human keratin fibers, such as hair.

The invention also relates to a composition for the oxidation-dyeing of keratin fibers, and in particular of human keratin fibers such as the hair, characterized in that it comprises, as oxidation-dye precursor, in a medium which is suitable for dyeing, at least one compound of formula (I), in accordance with the invention.

The compound(s) of formula (I) in accordance with the invention preferably represent(s) from 0.0005 to 12% by weight approximately relative to the total weight of the dye composition, and even more preferably from 0.005 to 6% by weight approximately relative to this weight.

The medium which is suitable for dyeing (or the support), generally comprises of water or a mixture of water and at least one organic solvent to dissolve the compounds which would not be sufficiently soluble in water. Examples of organic solvents may include, but are not limited to, $(C_1–C_4)$ lower alkanols, such as ethanol and isopropanol; glycerol; glycols and glycol ethers, such as 2-butoxyethanol, propylene glycol, propylene glycol monomethyl ether, diethylene glycol monoethyl ether and monomethyl ether, as well as aromatic alcohols, such as benzyl alcohol or phenoxyethanol, similar products and mixtures thereof.

The solvents may be present in proportions preferably ranging from 1 to 40% by weight approximately relative to the total weight of the dye composition, and even more preferably ranging from 5 to 30% by weight approximately.

The pH of the dye composition, in accordance with the invention, ranges from 3 to 12 approximately, and preferably ranges from 5 to 11 approximately. It can be adjusted to the desired value using acidifying or basifying agents commonly used to dye keratin fibers.

Examples of acidifying agents may include, but are not limited to, inorganic or organic acids, such as hydrochloric acid, orthophosphoric acid, sulphuric acid, and carboxylic acids, such as acetic acid, tartaric acid, citric acid and lactic acid, and sulphonic acids.

Examples of basifying agents may include, but are not limited to, aqueous ammonia, alkaline carbonates, alkanolamines, such as mono-, di- and triethanolamine and derivatives thereof, sodium hydroxide, potassium hydroxide and the compounds of formula (V) below:

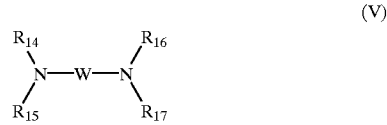

(V)

in which W is a propylene residue optionally substituted with a hydroxyl group or a $(C_1–C_6)$alkyl radical; $R_{14}$, $R_{15}$, $R_{16}$ and $R_{17}$, which may be identical or different, are chosen from a hydrogen atom, a $(C_1–C_6)$alkyl radical or a hydroxy $(C_1–C_6)$alkyl radical.

In addition to the compound(s) of formula (I) defined above, the dye composition, in accordance with the invention, can also contain at least one oxidation base which can be chosen from the oxidation bases conventionally used for oxidation-dyeing and may include, but are not limited to, para-phenylenediamines, bis(phenyl)alkylenediamines, para-aminophenols, ortho-aminophenols and heterocyclic bases.

Examples of para-phenylenediamines may include, but are not limited to, para-phenylenediamine, para-toluylenediamine, 2,6-dimethyl-para-phenylenediamine, 2-β-hydroxyethyl-para-phenylenediamine, 2-n-propyl-para-phenylenediamine, 2-isopropyl-para-phenylenediamine, N-(β-hydroxypropyl)-para-phenylenediamine, N,N-bis(β-hydroxyethyl)-para-phenylenediamine, 4-amino-N-(β-methoxyethyl)aniline, the para-phenylenediamines described in French patent application FR 2 630 438, the disclosure of which is hereby incorporated by reference, and acid addition salts thereof.

Examples of bis(phenyl)alkylenediamines may include, but are not limited to, N,N'-bis(b-hydroxyethyl)-N,N'-bis(4'-aminophenyl)-1,3-diaminopropanol, N,N'-bis(b-hydroxyethyl)-N,N'-bis(4'-aminophenyl)ethylenediamine, N,N'-bis (4-aminophenyl)tetramethylenediamine, N,N'-bis (b-hydroxyethyl)-N,N'-bis (4-aminophenyl) tetramethylenediamine, N,N'-bis (4-methylaminophenyl) tetramethylenediamine and N,N'-bis(ethyl)-N,N'-bis(4'-amino-3'-methylphenyl)ethylenediamine and acid addition salts thereof.

Examples of para-aminophenols may include, but are not limited to, para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethylaminomethyl)phenol and acid addition salts thereof.

Examples of ortho-aminophenols may include, but are not limited to, 2-aminophenol, 2-amino-5-methylphenol, 2-amino-6-methylphenol and 5-acetamido-2-aminophenol, and the acid addition salts thereof.

Examples of heterocyclic bases may include, but are not limited to, pyridine derivatives and pyrimidine derivatives that are non-cationic, and pyrazole derivatives.

Examples of pyridine derivatives may include, but are not limited to the compounds described, for example, in GB patents 1 026 978 and 1 153 196, the disclosures of which are hereby incorporated by reference, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and acid addition salts thereof.

Examples of pyrimidine derivatives may include, but are not limited to the compounds described, for example, in German patent DE 2 359 399, Japanese patents JP 88–169 571 and 91–10659, or patent application WO 96/15765, the disclosures of which are hereby incorporated by reference, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and pyrazolopyrimidine derivatives such as those mentioned in patent application FR-A-2 750 048, the disclosure of which is hereby incorporated by reference, and among which mention may be made of pyrazolo(1,5-a)pyrimidine-3,7-diamine; 2,5-dimethylpyrazolo(1,5-a)pyrimidine-3,7-diamine; pyrazolo (1,5-a)pyrimidine-3,5-diamine; 2,7-dimethylpyrazolo(1,5-a)pyrimidine-3,5-diamine; 3-aminopyrazolo(1,5-a) pyrimidin-7-ol; 3-aminopyrazolo(1,5-a)pyrimidin-5-0l; 2-(3-aminopyrazolo(1,5-a)pyrimidin-7-ylamino)ethanol, 2-(7-aminopyrazolo(1,5-a)pyrimidin-3-ylamino)ethanol, 2-((3-aminopyrazolo(1,5-a)pyrimidin-7-yl)-(2-hydroxyethyl)amino)ethanol, 2-((7-aminopyrazolo(1,5-a) pyrimidin-3-yl)-(2-hydroxyethyl)amino)ethanol, 5,6-dimethylpyrazolo(1,5-a)pyrimidine-3,7-diamine, 2,6-dimethylpyrazolo(1,5-a)pyrimidine-3,7-diamine, 2,5,N7, N7-tetramethylpyrazolo(1,5-a)pyrimidine-3,7-diamine and 3-amino-5-methyl-7-imidazolylpropylaminopyrazolo(1,5-a)pyrimidine, acid addition salts thereof and the tautomeric forms thereof when a tautomeric equilibrium exists.

Examples of pyrazole derivatives may include, but are not limited to the compounds described in patents DE 3 843 892 and DE 4 133 957 and patent applications WO 94/08969, WO 94/08970, FR-A-2 733 749 and DE 195 43 988, the disclosures of all of which are hereby incorporated by reference, such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl- 3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl) amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl) amino-1-methylpyrazole, and acid addition salts thereof.

When they are used, these oxidation bases preferably represent from 0.0005 to 12% by weight approximately relative to the total weight of the dye composition and even more preferably from 0.005 to 6% approximately relative to this weight.

The oxidation-dye compositions, in accordance with the invention, may also comprise at least one coupler and/or at least one direct dye, in particular to modify the shades or to enrich them with glints.

The couplers, which can be used in the oxidation-dye compositions, in accordance with the invention, may be chosen from the couplers conventionally used for oxidation-dyeing and may include, but are not limited to, meta-phenylenediamines, meta-aminophenols, meta-diphenols and heterocyclic couplers such as, for example, indole derivatives, indoline derivatives, pyridine derivatives, pyrazoloazoles and pyrazolones, and acid addition salts thereof.

These couplers may also be chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one and 3,6-dimethylpyrazolo (3,2-c)-1,2,4-triazole, and acid addition salts thereof.

When they are present, these couplers preferably represent from 0.0001 to 10% by weight approximately relative to the total weight of the dye composition and even more preferably from 0.005 to 5% by weight approximately relative to this weight.

In general, acid addition salts, which can be used in the context of the invention (compounds of formula (I), oxidation bases and couplers), may be chosen from hydrochlorides, hydrobromides, sulphates, citrates, succinates, tartrates, lactates and acetates.

The dye composition, in accordance with the invention, may also comprise various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetration agents, sequestering agents, fragrances, buffers, dispersing agents, packaging agents, such as, for example, silicones, film-forming agents, preserving agents and opacifiers.

One of ordinary skill in the art will know how to select this or these optional additional compounds such that the advantageous properties intrinsically associated with the oxidation-dye composition, in accordance with the invention, are not, or are not substantially, adversely affected by the addition(s) envisaged.

The dye composition, according to the invention, may be in various forms, such as in the form of liquids, creams or gels, or in any other form which is suitable for dyeing keratin fibers, in particular human hair.

The invention also relates to a process for dyeing keratin fibers, in particular human keratin fibers, such as hair, using the dye composition, as defined above.

According to this process, at least one dye composition, as defined above, is applied to the fibers for a period which is sufficient to develop the desired coloration, either in air or using an oxidizing agent. The dye composition may optionally comprise oxidation catalysts, in order to accelerate the oxidation process.

According to a first embodiment of the process of the invention, the coloration of the fibers may be carried out without addition of an oxidizing agent, merely on contact with atmospheric oxygen.

According to a second embodiment of the process of the invention, in particular when the dye composition, in accordance with the invention, comprises one or more oxidation bases and/or one or more couplers, at least one dye composition, as defined above, is applied to the fibers, the color being developed at acidic, neutral or alkaline pH using an oxidizing agent which is added to the dye composition just at the time of use, or which is present in an oxidizing composition which is applied simultaneously or sequentially in a separate manner.

According to this second embodiment of the dyeing process of the invention, the dye composition, described above, is preferably mixed, at the time of use, with an oxidizing composition comprising, in a medium which is suitable for dyeing, at least one oxidizing agent present in an amount which is sufficient to develop a coloration. The mixture obtained is then applied to the keratin fibers and is left in place for 3 to 50 minutes approximately, preferably 5 to 30 minutes approximately, after which the fibers are rinsed, washed with shampoo, rinsed again and dried.

The oxidizing agent present in the oxidizing composition, as defined above, may be chosen from the oxidizing agents conventionally used for the oxidation-dyeing of keratin fibers, and may include, but are not limited to, hydrogen peroxide, urea peroxide, alkali metal bromates and persalts, such as perborates and persulphates, and enzymes, such as peroxidases, laccases, tyrosinases and oxidoreductases, which may include, but are not limited to, pyranose oxidases, glucose oxidases, glycerol oxidases, lactate oxidases, pyruvate oxidases and uricases.

The pH of the oxidizing composition comprising the oxidizing agent, as defined above, is such that, after mixing with the dye composition, the pH of the resultant composition applied to the keratin fibers preferably varies from 3 to 12 approximately, and even more preferably from 5 to 11. It is adjusted to the desired value using acidifying or basifying agents commonly used to dye keratin fibers and as defined above.

The oxidizing composition, as defined above, may also comprise various adjuvants conventionally used in compositions for dyeing the hair and as defined above.

The composition, which is finally applied to the keratin fibers, may be in various forms, such as in the form of liquids, creams, gels or any other form which is suitable for dyeing keratin fibers, in particular human hair.

Another subject of the invention is a multi-compartment dyeing device or "kit" or any other multi-compartment packaging system, a first compartment of which contains the dye composition, as defined above, and a second compartment of which comprises the oxidizing composition, as defined above. These devices can be equipped with a means for delivering the desired mixture onto the hair, such as the devices described in patent FR 2,586,913, the disclosure of which is hereby incorporated by reference.

The examples which follow are intended to illustrate the invention without, however, limiting its scope.

PREPARATION EXAMPLES

Preparation Example 1

Synthesis of 1-(2-(2-amino-4-hydroxyphenylamino) ethyl)-3-methyl-3H-imidazol-1-ium chloride dihydrochloride

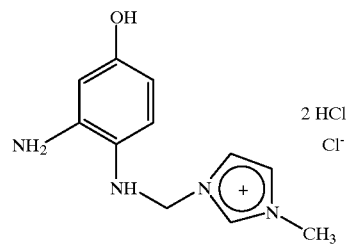

a) Preparation of 2-(4-benzyloxy-2-nitrophenylamino) ethanol

A suspension of 115 g (0.58 mol) of 4-(2-hydroxyethylamino)-3-nitrophenol (RN 65235-31-6) and 96.2 g (0.696 mol) of potassium carbonate in 350 ml of dimethylformamide was prepared and heated in a boiling water bath.

73.6 ml (0.638 mol) of benzyl chloride were added dropwise over 20 minutes and heating was continued for 3 hours in a boiling water bath.

The resulting mixture was poured into 2 litres of ice-cold water and the crystalline product was spin-dried and reslurried in water.

After recrystallization from refluxing 96° ethanol, 145 g of red-brown crystals of 2-(4-benzyloxy-2-nitrophenylamino)ethanol melting at 112° C. (Kofler) were obtained, the elemental analysis of which, calculated for $C_{15}H_{16}N_2O_4$, was:

| %          | C     | H    | N    | O     |
|------------|-------|------|------|-------|
| Calculated | 62.49 | 5.59 | 9.72 | 22.20 |
| Found      | 62.45 | 5.61 | 9.60 | 22.35 | b) Preparation of (4-benzyloxy-2-nitrophenyl)-(2-chloroethyl)amine 144.5 g (0.5 mol) of 2-(4-benzyloxy-2-nitrophenylamino) ethanol obtained above in the previous step and 97 ml of triethylamine (0.7 mol) were dissolved in 750 ml of dimethylformamide and cooled to 0° C.

58.0 ml (0.6 mol) of methanesulphonyl chloride were added dropwise over 40 minutes while maintaining the temperature between 0 and 5° C.

The resulting mixture was stirred at a temperature of 0° C. for a further 30 minutes.

63.5 g (1.5 mol) of lithium chloride were added and the mixture was placed in a boiling water bath for 15 minutes.

The resulting mixture was poured into 2.5 litres of ice-cold water and an oily precipitate crystallized slowly.

This product was spin-dried, reslurried in water and dried.

After recrystallization from refluxing isopropyl acetate, 102.3 g of brick-coloured crystals of (4-benzyloxy-2-nitrophenyl)-(2-chloroethyl)amine melting at 83° C. (Kofler) were obtained, the elemental analysis of which, calculated for $C_{15}H_{15}N_2O_3Cl$, was:

| %          | C     | H    | N    | O     | Cl    |
|------------|-------|------|------|-------|-------|
| Calculated | 58.73 | 4.93 | 9.13 | 15.91 | 11.56 |
| Found      | 58.67 | 4.84 | 9.13 | 15.65 | 11.20 | c) Preparation of 1-(2-(4-benzyloxy-2-nitrophenylamino) ethyl)-3-methyl-3H-imidazol-1-ium chloride monohydrate 30.6 g (0.1 mol) of (4-benzyloxy-2-nitrophenyl)-(2-chloroethyl)amine obtained above in the previous step and 24.6 g (0.3 mol) of 1-methyl-1H-imidazole (RN 616-47-7) in 60 ml of toluene were refluxed for 12 hours.

The resulting mixture was cooled and the crystalline precipitate was spin-dried and reslurried in ethyl acetate.

After recrystallization from refluxing absolute ethanol, 27.2 g of orange-red crystals of 1-(2-(4-benzyloxy-2-nitrophenylamino)ethyl)-3-methyl-3H-imidazol-1-ium chloride monohydrate melting at 145° C. (Kofler) were obtained, the elemental analysis of which, calculated for $C_{19}H_{21}N_4O_3Cl.H_2O$, was:

| %          | C     | H    | N     | O     | Cl   |
|------------|-------|------|-------|-------|------|
| Calculated | 56.09 | 5.70 | 13.77 | 15.73 | 8.71 |
| Found      | 57.29 | 5.69 | 13.88 | 15.10 | 8.66 | d) Reduction and debenzylation of 1-(2-(4-benzyloxy-2-nitrophenylamino)ethyl)-3-methyl-3H-imidazol-1-ium chloride monohydrate 15.3 g (0.0376 mol) of 1-(2-(4-benzyloxy-2-nitrophenylamino)ethyl)-3-methyl-3H-imidazol-1-ium chloride monohydrate obtained above in the previous step, 5 g of 5% palladium-on-charcoal (containing 50% water), 150 ml of 96° ethanol and 150 ml of water were placed in a hydrogenator.

The reduction took place in ½ hour at a hydrogen pressure of about 8 bar and at a temperature which was gradually raised to 45° C. After filtering off the catalyst under nitrogen, the filtrate was poured into 25 ml of 36% hydrochloric acid and evaporated to dryness under reduced pressure.

After recrystallization from a refluxing ethanol/water mixture and drying at 40° C. under vacuum and over potassium hydroxide, 8.0 g of beige-coloured crystals of 1-(2-(2-amino-4-hydroxyphenylamino)ethyl)-3-methyl-3H-imidazol-1-ium chloride dihydrochloride melting with decomposition at 220–222° C. (Kofler) were obtained, the elemental analysis of which, calculated for $C_{12}H_{19}N_4OCl_3$, was:

| %          | C     | H    | N     | O    | Cl    |
|------------|-------|------|-------|------|-------|
| Calculated | 42.19 | 5.61 | 16.40 | 4.68 | 31.13 |
| Found      | 41.95 | 5.69 | 16.13 | 5.63 | 30.62 |

Preparation Example 2

Synthesis of 1-{2-((3-amino-4-methylaminophenyl) methylamino)ethyl}-3-methyl-3H-imidazol-1-ium chloride dihydrochloride

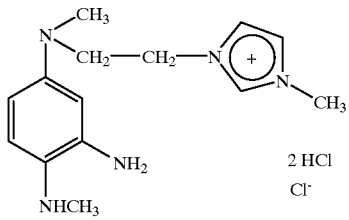

a) Preparation of 3-methyl-1-{2-(methyl-(4-methylamino-3-nitrophenyl)amino)ethyl}-3H-imidazol-1-ium chloride monohydrate A suspension of 41.4 g (0.17 mol) of N4-(2-chloroethyl)-N1,N4-dimethyl-2-nitrobenzene-1,4-diamine (RN 14607-54-6) obtained above in the previous step and 41.8 g (0.51 mol) of 1-methyl-1H-imidazole (RN 616-47-7) in 100 ml of toluene was prepared.

This suspension was heated with stirring at the reflux point of the toluene for 4 hours and the boiling product was spin-dried and reslurried twice in ethyl acetate and then in absolute ethanol.

After drying at 40° C. under vacuum, 37.8 g of violet crystals of 3-methyl-1-{2-(methyl-(4-methylamino-3-nitrophenyl)amino)ethyl}-3H-imidazol-1-ium chloride monohydrate melting at 135° C. (Kofler) were obtained, the elemental analysis of which, calculated for $C_{14}H_{20}N_5O_2Cl.H_2O$, was:

| %          | C     | H    | N     | O     | Cl    |
|------------|-------|------|-------|-------|-------|
| Calculated | 48.91 | 6.45 | 20.37 | 13.96 | 10.31 |
| Found      | 48.65 | 6.50 | 20.29 | 14.00 | 10.28 | b) Reduction of 3-methyl-1-{2-(methyl-(4-methylamino-3-nitrophenyl)amino)ethyl}-3H-imidazol-1-ium chloride monohydrate 19.5 g (0.0567 mol) of 3-methyl-1-{2-(methyl-(4-methylamino-3-nitrophenyl)amino)ethyl}-3H-imidazol-1-ium chloride monohydrate obtained above in the previous step, 10 g of 5% palladium-on-charcoal (containing 50% water), 200 ml of 96° ethanol and 200 ml of water were placed in a hydrogenator.

The reduction took place in ½ hour at a hydrogen pressure of about 9 bar and at a temperature which was gradually raised to 50° C. After filtering off the catalyst under nitrogen, the filtrate was poured into 20 ml of 36% hydrochloric acid and evaporated to dryness under reduced pressure.

The compound was taken up several times in absolute ethanol. After recrystallization from a refluxing ethanol/water mixture and drying at 40° C. under vacuum and over potassium hydroxide, 8.0 g of pale grey crystals of 1-{2-((3-amino-4-methylaminophenyl)methylamino)ethyl}-3-methyl-3H-imidazol-1-ium chloride dihydrochloride melting with decomposition at 240–242° C. (Kofler) were obtained. The proton NMR spectrum of which was in accordance with the proposed structure.

APPLICATION EXAMPLES

Examples 1 to 8 of Dyeing in Alkaline Medium

The dye compositions below, in accordance with the invention, were prepared (contents in grams):

| EXAMPLE | 1 | 2 | 3 | 4 | 5 | 6 | 7 | 8 |
|---|---|---|---|---|---|---|---|---|
| 1-(2-(2-Amino-4-hydroxy-phenylamino)ethyl)-3-methyl-3H-imidazol-1-ium chloride dihydrochloride (compound of formula (I)) | 1.02 | 1.02 | 1.02 | 1.02 | 1.02 | 1.02 | 1.02 | 1.02 |
| para-toluylenediamine (oxidation base) | 0.33 | — | — | — | — | — | — | — |
| para-aminophenol (oxidation base) | — | 0.327 | — | — | — | — | — | — |
| Pyrazolo-(1,5-a)pyrimidine-3,7-diamine dihydrochloride (oxidation base) | — | — | 0.666 | — | — | — | — | — |
| 1,3-dihydroxybenzene (coupler) | — | — | — | 0.33 | — | — | — | — |
| 3-aminophenol (coupler) | — | — | — | — | 0.327 | — | — | — |
| 5-N-(β-Hydroxyethyl)amino-2-methylphenol (coupler) | — | — | — | — | — | 0.498 | — | — |
| 2,4-diamino-1-(β-hydroxy-ethyloxy)benzene dihydrochloride (coupler) | — | — | — | — | — | — | 0.723 | — |
| 3,6-dimethylpyrazolo(3,2-c)-1,2,4-triazole (coupler) | — | — | — | — | — | — | — | 0.42 |
| Common dye support No. 1 | (*) | (*) | (*) | (*) | (*) | (*) | (*) | (*) |
| Demineralized water qs | 100 g | 100 g | 100 g | 100 g | 100 g | 100 g | 100 g | 100 g |

| (*) Common dye support No. 1: | |
|---|---|
| -96° ethyl alcohol | 18 g |
| -Sodium metabisulphite as an aqueous 35% solution | 0.68 g |
| -Pentasodium salt of diethylenetriamine-pentaacetic acid | 1.1 g |
| -20% aqueous ammonia | 10.0 g |

At the time of use, each of the above dye compositions were mixed, weight for weight with a 20-volume hydrogen peroxide solution (6% by weight) of pH 3.

The mixtures obtained were applied to locks of natural grey hair containing 90% white hairs, for 30 minutes. The locks were then rinsed, washed with a standard shampoo, rinsed again and then dried.

The shades obtained are given in the table below:

| EXAMPLE | Dyeing pH | Shade obtained |
|---|---|---|
| 1 | 10 ± 0.2 | Iridescent golden dark blond |
| 2 | 10 ± 0.2 | Coppery golden dark blond |
| 3 | 10 ± 0.2 | Coppery iridescent light chestnut |
| 4 | 10 ± 0.2 | Coppery iridescent dark blond |
| 5 | 10 ± 0.2 | Coppery iridescent dark blond |
| 6 | 10 ± 0.2 | Golden iridescent dark blond |
| 7 | 10 ± 0.2 | Matet ash dark blond |
| 8 | 10 ± 0.2 | Iridescent golden dark blond |

Examples 9 to 16 of Dyeing in Alkaline Medium

The dye compositions below, in accordance with the invention, were prepared (contents in grams):

| EXAMPLE | 9 | 10 | 11 | 12 | 13 | 14 | 15 | 16 |
|---|---|---|---|---|---|---|---|---|
| 1-{2-[(3-Amino-4-methyl-aminophenyl)methylamino]-ethyl}-3-methyl-3H-imidazol-1-ium chloride dihydrochloride (compound of formula (I)) | 1.11 | 1.11 | 1.11 | 1.11 | 1.11 | 1.11 | 1.11 | 1.11 |
| para-toluylenediamine (oxidation base) | 0.33 | — | — | — | — | — | — | — |
| para-aminophenol (oxidation base) | — | 0.327 | — | — | — | — | — | — |
| Pyrazolo-[1,5-a]pyrimidine-3,7-diamine dihydrochloride (oxidation base) | — | — | 0.666 | — | — | — | — | — |
| 1,3-dihydroxybenzene (coupler) | — | — | — | 0.33 | — | — | — | — |
| 3-aminophenol (coupler) | — | — | — | — | 0.327 | — | — | — |
| 5-N-(b-Hydroxyethyl)amino-2-methylphenol (coupler) | — | — | — | — | — | 0.498 | — | — |
| 2,4-diamino-1-(b-hydroxy-ethyloxy)benzene dihydrochloride (coupler) | — | — | — | — | — | — | 0.723 | — |

-continued

| EXAMPLE | 9 | 10 | 11 | 12 | 13 | 14 | 15 | 16 |
|---|---|---|---|---|---|---|---|---|
| 3,6-dimethylpyrazolo[3,2-c]-1,2,4-triazole (coupler) | — | — | — | — | — | — | — | 0.42 |
| Common dye support No. 1 | (*) | (*) | (*) | (*) | (*) | (*) | (*) | (*) |
| Demineralized water qs | 100 g | 100 g | 100 g | 100 g | 100 g | 100 g | 100 g | 100 g |

| (*) Common dye support No. 1: | |
|---|---|
| -96° ethyl alcohol | 18 g |
| -Sodium metabisulphite as an aqueous 35% solution | 0.68 g |
| -Pentasodium salt of diethylenetriaminepentaacetic acid | 1.1 g |
| -20% aqueous ammonia | 10.0 g |

At the time of use, each of the above dye compositions were mixed, weight for weight, with a 20-volume hydrogen peroxide solution (6% by weight) of pH 3.

The mixtures obtained were applied to locks of natural grey hair containing 90% white hairs, for 30 minutes. The locks were then rinsed, washed with a standard shampoo, rinsed again and then dried.

The shades obtained are given in the table below:

| EXAMPLE | Dyeing pH | Shade obtained |
|---|---|---|
| 9 | 10 ± 0.2 | Coppery iridescent dark blond |
| 10 | 10 ± 0.2 | Iridescent coppery blond |
| 11 | 10 ± 0.2 | Iridescent ash light chestnut |
| 12 | 10 ± 0.2 | Mahogany iridescent blond |
| 13 | 10 ± 0.2 | slightly iridescent ash light chestnut |
| 14 | 10 ± 0.2 | Bluish ash light chestnut |
| 15 | 10 ± 0.2 | Bluish ash light chestnut |
| 16 | 10 ± 0.2 | Mahogany iridescent blond |

What is claimed is:

1. A compound of formula (I) below, and acid addition salts thereof:

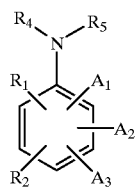

(I)

in which:

$A_1$, $A_2$ and $A_3$, which may be identical or different, are chosen from a group —$NR_7R_8$ and a hydroxyl radical; one and only one of the groups $A_1$, $A_2$ and $A_3$ may also represent a group $R_3$ as defined below;

$R_1$, $R_2$ and $R_3$, which may be identical or different, are chosen from a hydrogen atom; a halogen atom; a group Z as defined below; a ($C_1$–$C_6$)alkylcarbonyl radical; an amino($C_1$–$C_6$)alkylcarbonyl radical; an N—Z-amino ($C_1$–$C_6$)alkylcarbonyl radical; an N—($C_1$–$C_6$)alkylamino($C_1$–$C_6$)alkylcarbonyl radical; an N,N-di ($C_1$–$C_6$)-alkylamino ($C_1$–$C_6$)alkylcarbonyl radical; an amino($C_1$–$C_6$)alkylcarbonyl($C_1$–$C_6$)alkyl radical; an N—Z-amino($C_1$–$C_6$)alkylcarbonyl($C_1$–$C_6$)alkyl radical; an N—($C_1$–$C_6$)alkylamino($C_1$–$C_6$)alkylcarbonyl ($C_1$–$C_6$)alkyl radical; an N,N-di($C_1$–$C_6$)alkylamino ($C_1$–$C_6$)alkylcarbonyl($C_1$–$C_6$)alkyl radical; a carboxyl radical; a ($C_1$–$C_6$)alkylcarboxyl radical; a ($C_1$–$C_6$) alkylsulphonyl radical; an aminosulphonyl radical; an N—Z-aminosulphonyl radical; a ($C_1$–$C_6$)N-alkylaminosulphonyl radical; an N,N-di($C_1$–$C_6$) alkylaminosulphonyl radical; a ($C_1$–$C_6$) aminosulphonylalkyl radical; a ($C_1$–$C_6$)N—Z-aminosulphonylalkyl radical; an N—($C_1$–$C_6$) alkylaminosulphonyl($C_1$–$C_6$)alkyl radical; an N,N-di ($C_1$–$C_6$)-alkylaminosulphonyl($C_1$–$C_6$)alkyl radical; a carbamyl radical; an N—($C_1C_6$)alkylcarbamyl radical, an N,N-di($C_1$–$C_6$)alkylcarbamyl radical; a carbamyl ($C_1$–$C_6$)alkyl radical; an N—($C_1$–$C_6$)alkylcarbamyl ($C_1$–$C_6$)alkyl radical; an N,N-di($C_1$–$C_6$)alkylcarbamyl ($C_1$–$C_6$)alkyl radical; a ($C_1$–$C_6$)alkyl radical; a ($C_1$–$C_6$) monohydroxyalkyl radical; a ($C_2$–$C_6$) polyhydroxyalkyl radical; a ($C_1$–$C_6$)alkoxy($C_1$–$C_6$) alkyl radical; a ($C_1$–$C_6$)trifluoroalkyl radical; a cyano radical; a group $OR_6$ or $SR_6$; an amino group protected by a ($C_1$–$C_6$)alkylcarbonyl, ($C_1$–$C_6$)alkylcarboxyl, trifluoro($C_1$–$C_6$)alkylcarbonyl, amino($C_1$–$C_6$) alkylcarbonyl, N—Z-amino($C_1$–$C_6$)alkylcarbonyl, N—($C_1$–$C_6$)alkylamino($C_1$–$C_6$)alkylcarbonyl, N,N-di ($C_1$–$C_6$)alkylamino($C_1$–$C_6$)alkylcarbonyl, ($C_1$–$C_6$) alkylcarboxyl, carbamyl, N—($C_1$–$C_6$)alkylcarbamyl, N,N-di($C_1$–$C_6$)alkylcarbamyl, ($C_1$–$C_6$)alkylsulphonyl, aminosulphonyl, N—Z-aminosulphonyl, ($C_1$–$C_6$)N-alkylaminosulphonyl, N,N-di($C_1$–$C_6$) alkylaminosulphonyl, thiocarbamyl or formyl radical, or with a group Z as defined below in which a linker arm D comprises a ketone function directly attached to the nitrogen atom of the amino group; and a ($C_1$–$C_6$) aminoalkyl radical in which the alkyl is unsubstituted or substituted with one or more hydroxyl radicals; a ($C_1$–$C_6$)aminoalkyl radical in which the alkyl is unsubstituted or substituted with one or more hydroxyl radicals and in which the amine is substituted with one or two radicals, which may be identical or different, chosen from alkyl, ($C_1$–$C_6$)monohydroxyalkyl, ($C_2$–$C_6$)polyhydroxyalkyl, ($C_1$–$C_6$)alkylcarbonyl, cartamyl, N—($C_1$–$C_6$)alkylcarbamyl, N,N-di($C_1$–$C_6$) alkylcarbamyl, $C_1$–$C_6$ alkylsulphonyl, formyl, trifluoro ($C_1$–$C_6$)-alkylcarbonyl, ($C_1$–$C_6$)alkylcarboxyl and thiocatamyl radicals, or from a group Z as defined below, or which may form, together with the nitrogen atom to which they are attached, a 5- or 6-membered ring which is carbon-based or which contains one or more hetero atoms;

$R_6$ is chosen from a ($C_1$–$C_6$)alkyl radical; a ($C_1$–$C_6$) monohydroxyalkyl radical; a ($C_2$–$C_6$)

polyhydroxyalkyl radical; a group Z as defined below; a ($C_1$–$C_6$)alkoxy($C_1$–$C_6$)alkyl radical; an aryl radical; a benzyl radical; a carboxy($C_1$–$C_6$)alkyl radical; a ($C_1$–$C_6$)alkylcarboxy($C_1$–$C_6$)alkyl radical; a cyano ($C_1$–$C_6$)alkyl radical; a carbamyl($C_1$–$C_6$)alkyl radical; an N—($C_1$–$C_6$)alkylcarbamyl($C_1$–$C_6$)alkyl radical; an N,N-di($C_1$–$C_6$)alkylcarbamyl($C_1$–$C_6$)alkyl radical; a ($C_1$–$C_6$)trifluoroalkyl radical; a ($C_1$–$C_6$) aminosulphonylalkyl radical; a ($C_1$–$C_6$)N—Z-aminosulphonylalkyl radical; an N—($C_1$–$C_6$) alkylaminosulphonyl($C_1$–$C_6$)alkyl radical; an N,N-di ($C_1$–$C_6$)alkylaminosulphonyl($C_1$–$C_6$)alkyl radical; a ($C_1$–$C_6$)alkylsulphinyl ($C_1$–$C_6$)alkyl radical; a ($C_1$–$C_6$) alkylsulphonyl($C_1$–$C_6$)alkyl radical; a ($C_1$–$C_6$) alkylcarbonyl ($C_1$–$C_6$)alkyl radical; a ($C_1$–$C_6$) aminoalkyl radical in which the alkyl is unsubstituted or substituted with one or more hydroxyl radicals; and a ($C_1$–$C_6$)aminoalkyl radical in which the alkyl is unsubstituted or substituted with one or more hydroxyl radicals and in which the amine is substituted with one or two identical or different radicals chosen from ($C_1$–$C_6$)alkyl, ($C_1$–$C_6$)monohydroxyalkyl, ($C_2$–$C_6$) polyhydroxyalkyl, ($C_1$–$C_6$)allkylcarbonyl, formyl, trifluoro($C_1$–$C_6$)alkylcarbonyl, ($C_1$–$C_6$)alkylcarboxyl, carbamyl, N—($C_1$–$C_6$)alkylcarbamyl, N,N-di($C_1$–$C_6$) alkylcarbamyl, thiocarbamyl and ($C_1$–$C_6$) alkylsulphonyl radicals, or from a group Z as defined below; or which may form, together with the nitrogen atom to which they are attached, a 5- or 6-membered ring which is carbon-based or which contains one or more hetero atoms;

$R_4$, $R_5$, $R_7$ and $R_8$, which may be Identical or different, are chosen from a hydrogen atom; a group Z as defined below, in which the linker arm D contains no ketone functions directly linked to the nitrogen atom bearing the radicals $R_4$ and $R_5$; a ($C_1$–$C_6$)alkyl radical; a ($C_1$–$C_6$)monohydroxyalkyl radical; a ($C_2$–$C_6$) polyhydroxyalkyl radical; a ($C_1$–$C_6$)alkoxy($C_1$–$C_6$) alkyl radical; an aryl radical; a benzyl radical; a cyano ($C_1$–$C_6$)alkyl radical; a carbamyl($C_1$–$C_6$)alkyl radical; an N—($C_1$–$C_6$)alkylcarbamyl($C_1$–$C_6$)alkyl radical; an N,N-di($C_1$–$C_6$)alkylcarbamyl($C_1$–$C_6$)alkyl radical; a thiocarbamyl($C_1$–$C_6$)alkyl radical; a ($C_1$–$C_6$) trifluoroalkyl radical; a ($C_1$–$C_6$)sulphoalkyl radical; a ($C_1$–$C_6$)alkylcarboxy($C_1$–$C_6$)alkyl radical, a ($C_1$–$C_6$) alkylsulphinyl($C_1$–$C_6$)alkyl radical; a ($C_1$–$C_6$) aminosulphonylalkyl radical; a ($C_1$–$C_6$)N—Z-aminosulphonylalkyl radical; an N—($C_1$–$C_6$) alkylaminosulphonyl($C_1$–$C_6$)alkyl radical; an N,N-di ($C_1$–$C_6$)alkylaminosulphonyl($C_1$–$C_6$)alkyl radical; a ($C_1$–$C_6$)alkylcarbonyl($C_1$–$C_6$)alkyl radical; a ($C_1$–$C_6$) aminoalkyl radical in which the alkyl is unsubstituted or substituted with one or more hydroxyl radicals; and a ($C_1$–$C_6$)aminoalkyl radical in which the alkyl is unsubstituted or substituted with one or more hydroxyl radicals and in which the amine is substituted with one or two identical or different radicals chosen from ($C_1$–$C_6$)alkyl, ($C_1$–$C_6$)monohydroxyalkyl, ($C_2$–$C_6$) polyhydroxyalkyl, ($C_1$–$C_6$)alkylcarbonyl, carbamyl, N—($C_1$–$C_6$)alkylcarbamyl, N,N-di($C_1$–$C_6$) alkylcarbamyl, ($C_1$–$C_6$)alkylsulphonyl, formyl, trifluoro($C_1$–$C_6$)alkylcarbonyl, ($C_1$–$C_6$)alkylcarboxyl and thiocarbamyl radicals, or from a group Z as defined below; or which may form, together with the nitrogen atom to which they are attached, a 5- or 6-membered ring which is carbon-based or which contains one or more hetero atoms;

Z is chosen from the unsaturated cationic groups of formulae (II) and (III) below, and the saturated cationic groups of formula (IV) below:

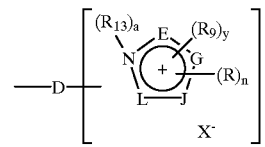

(II)

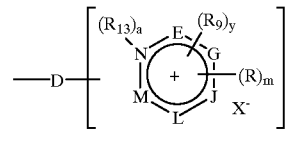

(III)

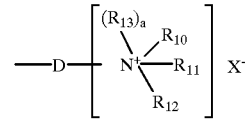

(IV)

in which:

D is a linker arm which represents a linear or branched alkyl chain, which can be interrupted by one or more hetero atoms, and which can be substituted with one or more hydroxyl or $C_1$–$C_6$ alkoxy radicals, and which can bear one or more ketone functions;

the ring members E, G, J, L and M, which may be identical or different, are chosen from a carbon, oxygen, sulphur and nitrogen;

n is an integer ranging from 0 to 4;

m is an integer ranging from 0 to 5;

the R radical, which may be identical or different, are chosen from a second Z group, which is identical to or different from the first Z group, a halogen atom, a hydroxyl radical, a ($C_1$–$C_6$)alkyl radical, a ($C_1$–$C_6$) monohydroxyalkyl radical, a ($C_2$–$C_6$) polyhydroxyalkyl radical, a nitro radical, a cyano radical, a cyano($C_1$–$C_6$)alkyl radical, a ($C_1$–$C_6$)alkoxy radical, a tri($C_1$–$C_6$)alkylsilane($C_1$–$C_6$)alkyl radical, an amido radical, a formyl radical, a carboxyl radical, a ($C_1$–$C_6$)alkylcarbonyl radical, a thio radical, a ($C_1$–$C_6$) thioalkyl radical, a ($C_1$–$C_6$)alkylthio radical, an amino radical, an amino radical protected with a ($C_1$–$C_6$) alkylcarbonyl, carbamyl or ($C_1$–$C_6$)alkylsulphonyl radical; a group NHRO or NROR″ in which RO and R″, which may be identical or different, are chosen from a ($C_1$–$C_6$)alkyl radical, a ($C_1$–$C_6$)monohydroxyalkyl radical and a ($C_2$–$C_6$)polyhydroxyalkyl radical;

$R_9$ is chosen from a ($C_1$–$C_6$)alkyl radical, a ($C_1$–$C_6$) monohydroxyalkyl radical, a ($C_2$–$C_6$) polyhydroxyalkyl radical, a cyano($C_1$–$C_6$)alkyl radical, a tri($C_1$–$C_6$)alkylsilane($C_1$–$C_6$)alkyl radical, a ($C_1$–$C_6$) alkoxy($C_1$–$C_6$)alkyl radical, a carbamyl-($C_1$–$C_6$)alkyl radical, a ($C_1$–$C_6$)alkylcarboxy($C_1$–$C_6$)-alkyl radical, a benzyl radical and a second Z group, which is identical to or different from the first Z group;

$R_{10}$, $R_{11}$ and $R_{12}$, which may be identical or different, are chosen from a ($C_1$–$C_6$)alkyl radical, a ($C_1$–$C_6$) monohydroxyalkyl radical, a ($C_2$–$C_6$) polyhydroxyalkyl radical, a ($C_1$–$C_6$)alkoxy($C_1$–$C_6$) alkyl radical, a cyano($C_1$–$C_6$)alkyl radical, an aryl radical, a benzyl radical, a ($C_1$–$C_6$)amidoalkyl radical, a tri($C_1$–$C_6$)alkylsilane($C_1$–$C_6$)alkyl radical and a ($C_1$–$C_6$)aminoalkyl radical in which the amine is protected by a (($C_1$–$C_6$)alkylcarbonyl, carbamyl or ($C_1$–$C_6$) alkylsulphonyl radical; two of the $R_{10}$, $R_{11}$ and $R_{12}$ radicals may also together form, with the nitrogen atom to which they are attached, a carbonaceous saturated 5- or 6-membered ring or which contains one or more hetero atoms, wherein said ring may be unsubstituted or substituted with a halogen atom, a hydroxyl radical, a ($C_1$–$C_6$)alkyl radical, a ($C_1$–$C_6$)monohydroxyalkyl radical, a ($C_2$–$C_6$)polyhydroxyalkyl radical, a nitro radical, a cyano radical, a cyano($C_1$–$C_6$)alkyl radical, a ($C_1$–$C_6$)alkoxy radical, a tri($C_1$–$C_6$)alkylsilane($C_1$–$C_6$) alkyl radical, an amido radical, a formyl radical, a carboxyl radical, a keto($C_1$–$C_6$)alkyl radical, a thio radical, a ($C_1$–$C_6$)thioalkyl radical, a ($C_1$–$C_6$)alkylthio radical, an amino radical or an amino radical protected with a ($C_1$–$C_6$)alkylcarbonyl, carbamyl or ($C_1$–$C_6$) alkylsulphonyl radical;

one of the $R_{10}$, $R_{11}$ and $R_{12}$ radicals may also be chosen from a second Z group which is identical to or different from the first Z group;

$R_{13}$ is chosen from a ($C_1$–$C_6$)alkyl radical; a ($C_1$–$C_6$) monohydroxy-alkyl radical; a ($C_2$–$C_6$) polyhydroxyalkyl radical; an aryl radical; a benzyl radical: a ($C_1$–$C_6$)aminoalkyl radical, a ($C_1$–$C_6$) aminoalkyl radical in which the amine is protected by a ($C_1$–$C_6$)alkylcarbonyl, carbamyl or ($C_1$–$C_6$) alkylsulphonyl radical; a carboxy($C_1$–$C_6$)alkyl radical; a cyano($C_1$–$C_6$)alkyl radical; a carbamyl($C_1$–$C_6$)alkyl radical a ($C_1$–$C_6$)trifluoroalkyl radical; a tri($C_1$–$C_6$) alkyolsilane-($C_1$–$C_6$)alkyl radical; a ($C_1$–$C_6$) sulphonamidoalkyl radical; a ($C_1$–$C_6$)alkylcarboxy ($C_1$–$C_6$)alkyl radical, a ($C_1$–$C_6$)alkylsulphinyl($C_1$–$C_6$) alkyl radical; a ($C_1$–$C_6$)alkylsulphonyl($C_1$–$C_6$)alkyl radical; a ($C_1$–$C_6$)alkylketo($C_1$–$C_6$)alkyl radical; an N—($C_1$–$C_6$)alkylcarbamyl($C_1$–$C_6$)alkyl radical, and an N—($C_1$–$C_6$)alkylsulphonamido($C_1$–$C_6$)alkyl radical;

a and y are integers equal to 0 or 1; with the following conditions;
  in the unsaturated cationic groups of formula (II):
  when a 0, the linker arm D is attached to the nitrogen atom,
  when a=1, the linker arm D is attached to one of the ring members E, G, J or L vertices,
  y can take the value 1 only:
    1) when the ring members E, G, J and L simultaneously represent a carbon atom and when the $R_9$ radical is carried by the nitrogen atom of the unsaturated ring; or alternatively
    2) when at least one of the ring members E, G, J and L represents a nitrogen atom to which the $R_9$ radical is attached;
  in the unsaturated cationic groups of formula (III):
  when a=0, the linker arm D is attached to the nitrogen atom,
  when a=1, the linker arm D is attached to one of the ring members E, G, J, L or M, y can take the value 1 only when at least one of the ring members E, G, J, L and M represents a divalent atom and when the $R_9$ radical is carried by the nitrogen atom of the unsaturated ring;
  in the cationic groups of formula (IV):
  when a=0, then the linker arm D is attached to the nitrogen atom carrying the $R_{10}$ to $R_{12}$ radicals,
  when a=1, then two of the $R_{10}$ to $R_{12}$ radicals form, together with the nitrogen atom to which they are attached, a saturated 5- or 6membered ring as defined above, and the linker arm D is carried by a carbon atom of the saturated ring;

$X^-$ is a monovalent or divalent anion; with the proviso that the number of cationic Z groups in the compound of formula (I) is at least equal to 1.

2. The compound according to claim 1, wherein in at least one of said formulae (II), (III), and (IV), D is a linear or branched alkyl chain containing from 1 to 14 carbon atoms.

3. The compound according to claim 1, wherein in at least one of said formulae (II), (III), and (IV), D can be interrupted by oxygen, sulphur, or nitrogen atoms.

4. The compound according to claim 1, wherein the rings of the unsaturated Z groups of formula (II) are chosen from pyrrole, imidazole, pyrazole, oxazole, thiazole and triazole rings.

5. The compound according to claim 1, wherein the rings of the unsaturated Z groups of formula (III) are chosen from pyridine, pyrimidine, pyrazine, oxazine and triazine rings.

6. The compound according to claim 1, wherein two of the $R_{10}$, $R_{11}$, and $R_{12}$ radicals form a pyrrolidine ring, a piperidine ring, a piperazine ring or a morpholine ring, it being possible for the ring to be unsubstituted or substituted with a halogen atom, a hydroxyl radical, a ($C_1$–$C_6$)alkyl radical, a ($C_1$–$C_6$)monohydroxyalkyl radical, a ($C_2$–$C_6$) polyhydroxyalkyl radical, a nitro radical, a cyano radical, a cyano ($C_1$–$C_6$)alkyl radical, a ($C_1$–$C_6$)alkoxy radical, a tri($C_1$–$C_6$) alkylsilane($C_1$–$C_6$)alkyl radical, an amido radical, a formyl radical, a carboxyl radical, a keto($C_1$–$C_6$)alkyl radical, a thio radical, a ($C_1$–$C_6$)thioalkyl radical, a ($C_1$–$C_6$)alkylthio radical, an amino radical or an amino radical protected by a ($C_1$–$C_6$)alkylcarbonyl, carbamyl or ($C_1$–$C_6$)alkylsulphonyl radical.

7. The compound according to claim 1, wherein $X^-$ is chosen from a halogen atom, a hydroxide, a hydrogen sulphate or a ($C_1$–$C_6$)alkyl sulphate.

8. The compound according to claim 1, wherein the compound is chosen from:
  1-(2-(2-amino-4-hydroxyphenylamino)ethyl)-3-methyl-3H-imidazol-1-ium chloride;
  1-{2-((3-amino-4-methylaminophenyl)methylamino) ethyl}-3-methyl-3H-imidazol-1-ium chloride;
  1-{2-((3-amino-4-methylaminophenyl)methylamino) ethyl}-1,4-dimethyl-1-piperazinium chloride;
  {2-((3-amino-4-methylaminophenyl)methylamino) ethyl}-triethylammonium chloride;
  1-(2-(2-amino-4-hydroxyphenylamino)ethyl)-1,4-dimethyl-1-piperazinium chloride;
  (2-{2-amino-4-(bis(2-hydroxyethyl)amino) phenylamino}-ethyl)diethylmethylammonium chloride;
  3-(3-{3-(3-(3-methyl-3H-imidazo1-ium)propylamino)-4-aminophenylamino}propyl)-1-methyl-3H-imidazol-1-ium dichloride;
  3-methyl-1-(2-(2,4,5-trihydroxyphenylamino)ethyl)-3H-imidazol-1-ium chloride;
  1-(2-(2-amino-5-ethoxy-4-hydroxyphenylamino)ethyl)-3-methyl-3H-imidazol-1-ium chloride;
  1-(2-(2-amino-5-hydroxy-4-methoxyphenylamino) ethyl)-3-methyl-3H-imidazol-1-ium chloride;
  1-(2-{4-amino-5-(2-(diethylmethylammonium) ethylamino)-2-hydroxyphenoxy}ethyl)-3-methyl-3H-imidazol-1-ium dichloride; and acid addition salts thereof.

9. The compound according to claim 1, wherein acid addition salts are chosen from hydrochlorides, hydrobromides, sulphates, citrates, succinates, tartrates, lactates and acetates.

10. A composition for the oxidation-dyeing of keratin fibers, comprising, in a medium which is suitable for dyeing, at least one compound of formula (I) or an acid addition salt thereof as an oxidation dye precursor:

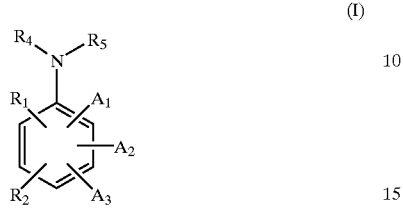

in which:
- $A_1$, $A_2$ and $A_3$, which may be identical or different, are chosen from a group —$NR_7R_8$ and a hydroxyl radical; one and only one of the groups $A_1$, $A_2$ and $A_3$ may also represent a group $R_3$ as defined below;
- $R_1$, $R_2$ and $R_3$, which may be identical or different, are chosen from a hydrogen atom; a halogen atom; a group Z as defined below; a $(C_1–C_6)$alkylcarbonyl radical; an amino$(C_1–C_6)$alkylcarbonyl radical; an N—Z-amino$(C_1–C_6)$alkylcarbonyl radical; an N—$(C_1–C_6)$alkylamino$(C_1–C_6)$alkylcarbonyl radical; an N,N-di$(C_1–C_6)$-alkylamino$(C_1–C_6)$alkylcarbonyl radical; an amino$(C_1–C_6)$alkylcarbonyl$(C_1–C_6)$alkyl radical; an N—Z-amino$(C_1–C_6)$alkylcarbonyl$(C_1–C_6)$alkyl radical; an N—$(C_1–C_6)$alkylamino$(C_1–C_6)$alkylcarbonyl$(C_1–C_6)$alkyl radical; an N,N-di$(C_1–C_6)$alkylamino$(C_1–C_6)$alkylcarbonyl$(C_1–C_6)$alkyl radical; a carboxyl radical; a $(C_1–C_6)$alkylcarboxyl radical; a $(C_1–C_6)$alkylsulphonyl radical; an aminosulphonyl radical; an N—Z-aminosulphonyl radical; a $(C_1–C_6)$N-alkylaminosulphonyl radical; an N,N-di$(C_1–C_6)$alkylaminosulphonyl radical; a $(C_1–C_6)$aminosulphonylalkyl radical; a $(C_1–C_6)$N—Z-aminosulphonylalkyl radical; an N—$(C_1–C_6)$alkylaminosulphonyl$(C_1–C_6)$alkyl radical; an N, N-di$(C_1–C_6)$-alkylaminosulphonyl$(C_1–C_6)$alkyl radical; a carbamyl radical; an N—$(C_1–C_6)$alkylcarbamyl radical; an N,N-di$(C_1–C_6)$alkylcarbamyl radical; a carbamyl$(C_1–C_6)$alkyl radical; an N—$(C_1–C_6)$alkylcarbamyl$(C_1–C_6)$alkyl radical; an N,N-di$(C_1–C_6)$alkylcarbamyl$(C_1–C_6)$alkyl radical; a $(C_1–C_6)$alkyl radical; a $(C_1–C_6)$monohydroxyalkyl radical; a $(C_2–C_6)$polyhydroxyalkyl radical; a $(C_1–C_6)$alkoxy$(C_1–C_6)$alkyl radical; a $(C_1–C_6)$trifluoroalkyl radical; a cyano radical; a group $OR_6$ or $SR_6$; an amino group protected by a $(C_1–C_6)$alkylcarbonyl, $(C_1–C_6)$alkylcarboxyl trifluoro$(C_1–C_6)$alkylcarbonyl, amino$(C_1–C_6)$alkylcarbonyl, N—Z-amino$(C_1–C_6)$alkylcarbonyl, N—$(C_1–C_6)$alkylamino$(C_1–C_6)$alkylcarbonyl, N,N-di$(C_1–C_6)$alkylamino$(C_1–C_6)$alkylcarbonyl, $(C_1–C_6)$alkylcarboxyl, carbamyl, N—$(C_1–C_6)$alkylcarbamyl, N,N-di$(C_1–C_6)$alkylcarbamyl, $(C_1–C_6)$alkylsulphonyl, aminosulphonyl, N—Z-aminosulphonyl, $(C_1–C_6)$N-alkylaminosulphonyl, N,N-di$(C_1–C_6)$-alkylaminosulphonyl, thiocarbamyl or formyl radical, or with a group Z as defined below in which a linker arm D comprises a ketone function directly attached to the nitrogen atom of the amino group; and a $(C_1–C_6)$aminoalkyl radical in which the alkyl is unsubstituted or substituted with one or more hydroxyl radicals; a $(C_1–C_6)$aminoalkyl radical in which the alkyl is unsubstituted or substituted with one or more hydroxyl radicals and in which the amine is substituted with one or two radicals, which may be identical or different, chosen from alkyl, $(C_1–C_6)$monohydroxyalkyl, $(C_2–C_6)$polyhydroxyalkyl, $(C_1–C_6)$alkylcarbonyl, carbamyl, N—$(C_1–C_6)$alkylcarbamyl, N,N-di$(C_1–C_6)$ alkylcarbamyl, $C_1–C_6$ alkylsulphonyl, formyl, trifluoro$(C_1–C_6)$-alkylcarbonyl, $(C_1–C_6)$alkylcarboxyl and thiocarbamyl radicals, or from a group Z as defined below, or which may form, together with the nitrogen atom to which they are attached, a 5- or 6-membered ring which is carbon based or which contains one or more hetero atoms;
- $R_6$ is chosen from a $(C_1–C_6)$alkyl radical; a $(C_1–C_6)$monohydroxyalkyl radical; a $(C_2–C_6)$polyhydroxyalkyl radical; a group Z as defined below; a $(C_1–C_6)$alkoxy$(C_1–C_6)$alkyl radical; an aryl radical; a benzyl radical; a carboxy$(C_1–C_6)$alkyl radical; a $(C_1–C_6)$alkylcarboxy$(C_1–C_6)$alkyl radical; a cyano$(C_1–C_6)$alkyl radical; a carbamyl$(C_1–C_6)$alkyl radical; an N—$(C_1–C_6)$alkylcarbamyl$(C_1–C_6)$alkyl radical; an N,N-di$(C_1–C_6)$alkylcarbamyl$(C_1–C_6)$alkyl radical; a $(C_1–C_6)$trifluoroalkyl radical; a $(C_1–C_6)$aminosulphonylalkyl radical; a $(C_1–C_6)$N—Z-aminosulphonylalkyl radical, an N—$(C_1–C_6)$alkylaminosulphonyl$(C_1–C_6)$alkyl radical; an $N_3$, N-di$(C_1–C_6)$alkylaminosulphonyl$(C_1–C_6)$alkyl radical; a $(C_1–C_6)$alkylsulphinyl $(C_1–C_6)$alkyl radical; a $(C_1–C_6)$alkylsulphonyl$(C_1–C_6)$alkyl radical; a $(C_{1–C6})$alkylcarbonyl $(C_1–C_6)$alkyl radical; a $(C_1–C_6)$aminoalkyl radical in which the alkyl is unsubstituted or substituted with one or more hydroxyl radicals; and a $(C_1–C_6)$aminoalkyl radical in which the alkyl is unsubstituted or substituted with one or more hydroxyl radicals and in which the amine is substituted with one or two identical or different radicals chosen from $(C_1–C_6)$alkyl, $(C_1–C_6)$monohydroxyalkyl, $(C_2–C_6)$polyhydroxyalkyl, $(C_1–C_6)$alkylcarbonyl, formyl, trifluoro$(C_1–C_6)$alkylcarbonyl, $(C_1–C_6)$alkylcarboxyl, carbamyl, N—$(C_1–C_6)$alkylcarbamyl, N,N-di$(C_1–C_6)$ alkylcarbamyl, thiocarbamyl and $(C_1–C_6)$ alkylsulphonyl radicals, or from a group Z as defined below; or which may form, together with the nitrogen atom to which they are attached, a 5- or 6-membered ring which is carbon-based or which contains one or more hetero atoms;
- $R_4$, $R_5$, $R_7$ and $R_8$, which may be identical or different, are chosen from a hydrogen atom; a group Z as defined below, in which the linker arm D contains no ketone functions directly linked to the nitrogen atom bearing the radicals $R_4$
  and $R_5$; a $(C_1–C_6)$alkyl radical; a $(C_1–C_6)$monohydroxyalkyl radical; a $(C_2–C_6)$polyhydroxyalkyl radical; a $(C_1–C_6)$alkoxy$(C_1–C_6)$alkyl radical; an aryl radical; a benzyl radical; a cyano$(C_1–C_6)$alkyl radical; a carbamyl$(C_1–C_6)$alkyl radical; an N—$(C_1–C_6)$alkylcarbamyl$(C_1–C_6)$alkyl radical; an N,N-di$(C_1–C_6)$alkylcarbamyl$(C_1–C_6)$alkyl radical; a thiocarbamyl$(C_1–C_6)$alkyl radical; a $(C_1–C_6)$trifluoroalkyl radical; a $(C_1–C_6)$sulphoalkyl radical; a $(C_1–C_6)$alkylcarboxy$(C_1–C_6)$alkyl radical; a $(C_1–C_6)$alkylsulphinyl$(C_1–C_6)$alkyl radical; a $(C_1–C_6)$aminosulphonylalkyl radical; a $(C_1–C_6)$N—Z-aminosulphonylalkyl radical; an N—$(C_1–C_6)$alkylaminosulphonyl$(C_1–C_6)$alkyl radical; an N,N-di ($C_1$–$C_6$)alkylaminosulphonyl($C_1$–$C_6$)alkyl radical; a ($C_1$–$C_6$)alkylcarbonyl($C_1$–$C_6$)alkyl radical; a ($C_1$–$C_6$) aminoalkyl radical in which the alkyl is unsubstituted or substituted with one or more hydroxyl radicals; and a ($C_1$–$C_6$)aminoalkyl radical in which the alkyl is unsubstituted or substituted with one or more hydroxyl radicals and in which the amine is substituted with one or two identical or different radicals chosen from ($C_1$–$C_6$)alkyl, ($C_1$–$C_6$)monohydroxyalkyl, ($C_2$–$C_6$) polyhydroxyalkyl, ($C_1$–$C_6$)alkylcarbonyl, carbamyl, N—($C_1$–$C_6$)alkylcarbamyl, N,N-di($C_1$–$C_6$) alkylcarbamyl, ($C_1$–$C_6$)alkylsulphonyl, formyl, trifluoro($C_1$–$C_6$)alkylcarbonyl, ($C_1$–$C_6$)alkylcarboxyl and thiocarbamyl radicals, or from a group Z as defined below; or which may form, together with the nitrogen atom to which they are attached, a 5- or 6-membered ring which is carbon-based or which contains one or more hetero atoms;

Z is chosen from the unsaturated cationic groups of formulae (II) and (III) below, and the saturated cationic groups of formula (IV) below:

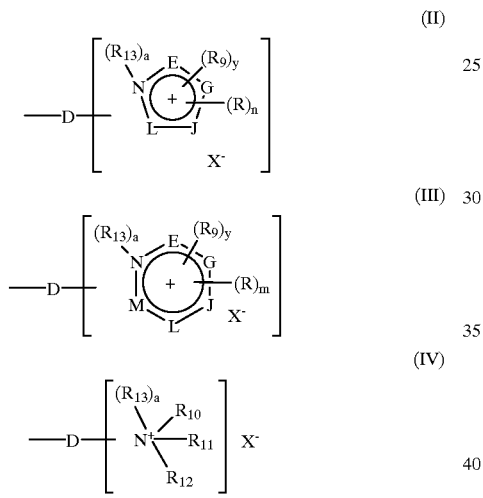

in which:
  D is a linker arm which represents a linear or branched alkyl chain, which can be interrupted by one or more hetero atoms, and which can be substituted with one or more hydroxyl or $C_1$–$C_6$ alkoxy radicals, and which can bear one or more ketone functions;
  the ring members E, G, J, L and M, which may be identical or different, are chosen from a carbon, oxygen, sulphur and nitrogen;
  n is an integer ranging from 0 to 4;
  m is an integer ranging from 0 to 5;
  the R radical, which may be identical or different, are chosen from a second Z group, which is identical to or different from the first Z group, a halogen atom, a hydroxyl radical, a ($C_1$–$C_6$)alkyl radical, a ($C_1$–$C_6$) monohydroxyalkyl radical, a ($C_2$–$C_6$) polyhydroxyalkyl radical, a nitro radical, a cyano radical, a cyano($C_1$–$C_6$)alkyl radical, a ($C_1$–$C_6$)alkoxy radical, a tri($C_1$–$C_6$)alkylsilane($C_1$–$C_6$)alkyl radical, an amido radical, a formyl radical, a carboxyl radical, a ($C_1$–$C_6$)alkylcarbonyl radical, a thio radical, a ($C_1$–$C_6$) thioalkyl radical, a ($C_1$–$C_6$)alkylthio radical, an amino radical, an amino radical protected with a ($C_1$–$C_6$) alkylcarbonyl, carbamyl or ($C_1$–$C_6$)alkylsulphonyl radical; a group NHRO or NROR″ in which RO and R″, which may be identical or different, are chosen from a ($C_1$–$C_6$)alkyl radical, a ($C_1$–$C_6$)monohydroxyalkyl radical and a ($C_2$–$C_6$)polyhydroxyalkyl radical;

$R_9$ is chosen from a ($C_1$–$C_6$)alkyl radical, a ($C_1$–$C_6$) monohydroxyalkyl radical, a ($C_2$–$C_6$) polyhydroxyalkyl radical, a cyano($C_1$–$C_6$)alkyl radical, a tri($C_1$–$C_6$)alkylsilane($C_1$–$C_6$)alkyl radical, a ($C_1$–$C_6$) alkoxy($C_1$–$C_6$)alkyl radical, a carbamyl-($C_1$–$C_6$)alkyl radical, a ($C_1$–$C_6$)alkylcarboxy($C_1$–$C_6$)-alkyl radical, a benzyl radical and a second Z group, which is identical to or different from the first Z group;

$R_{10}$, $R_{11}$ and $R_{12}$, which may be identical or different, are chosen from a ($C_1$–$C_6$)alkyl radical, a ($C_1$–$C_6$) monohydroxyalkyl radical, a ($C_2$$C_6$)polyhydroxyalkyl radical, a ($C_1$–$C_6$)alkoxy($C_1$–$C_6$)alkyl radical, a cyano ($C_1$–$C_6$)alkyl radical, an aryl radical, a benzyl radical, a ($C_1$–$C_6$)amidoalkyl radical, a tri($C_1$–$C_6$)alkylsilane ($C_1$–$C_6$)alkyl radical and a ($C_1$–$C_6$)aminoalkyl radical in which the amine is protected by a ($C_1$–$C_6$) alkylcarbonyl, carbamyl or ($C_1$–$C_6$)alkylsulphonyl radical; two of the $R_{10}$, $R_{11}$ and $R_{12}$ radicals may also together form, with the nitrogen atom to which they are attached, a carbonaceous saturated 5- or 6-membered ring or which contains one or more hetero atoms, wherein said ring may be unsubstituted or substituted with a halogen atom, a hydroxyl radical, a ($C_1$–$C_6$)alkyl radical, a ($C_1$–$C_6$)monohydroxyalkyl radical, a ($C_2$$C_6$) polyhydroxyalkyl radical, a nitro radical, a cyano radical, a cyano($C_1$–$C_6$)alkyl radical, a ($C_1$–$C_6$)alkoxy radical, a tri($C_1$–$C_6$)alkylsilane($C_1$–$C_6$)alkyl radical, an amido radical, a formyl radical, a carboxyl radical, a keto($C_1$–$C_6$)alkyl radical, a thio radical, a ($C_1$–$C_6$) thioalkyl radical, a ($C_1$–$C_6$)alkylthio radical, an amino radical or an amino radical protected with a ($C_1$–$C_6$) alkylcarbonyl, carbamyl or ($C_1$–$C_6$)alkylsulphonyl radical;

one of the $R_{10}$, $R_{11}$, and $R_{12}$ radicals may also be chosen from a second Z group which is identical to or different from the first Z group;

$R_{13}$ is chosen from a ($C_1$–$C_6$)alkyl radical; a ($C_1$–$C_6$) monohydroxy-alkyl radical; a ($C_2$–$C_6$) polyhydroxyalkyl radical; an aryl radical; a benzyl radical; a ($C_1$–$C_6$)aminoalkyl radical, a ($C_1$–$C_6$) aminoalkyl radical in which the amine is protected by a ($C_1$–$C_6$)alkylcarbonyl, carbamyl or ($C_1$–$C_6$) alkylsulphonyl radical; a carboxy($C_1$–$C_6$)alkyl radical; a cyano($C_1$–$C_6$)alkyl radical; a carbamyl($C_1$–$C_6$)alkyl radical; a ($C_1$–$C_6$)trifluoroalkyl radical; a tri($C_1$–$C_6$) alkylsilane-($C_1$–$C_6$)alkyl radical; a ($C_1$–$C_6$) sulphonamidoalkyl radical; a ($C_1$–$C_6$)alkylcarboxy ($C_1$–$C_6$)alkyl radical; a ($C_1$–$C_6$)alkylsulphinyl($C_1$–$C_6$) alkyl radical; a ($C_1$–$C_6$)alkylsulphonyl($C_1$–$C_6$)alkyl radical; a ($C_1$–$C_6$)alkylketo($C_1$–$C_6$)alkyl radical, an N—($C_1$–$C_6$)alkylcarbamyl($C_1$–$C_6$)alkyl radical; and an N—($C_1$–$C_6$)alkylsulphonamido($C_1$–$C_6$)alkyl radical;

a and y are integers equal to 0 or 1; with the following conditions:
  in the unsaturated cationic groups of formula (II):
  when a=0, the linker arm D is attached to the nitrogen atom,
  when a=1, the linker arm D is attached to one of the ring members E, G, J or L,
  y can take the value 1 only:
    1) when the ring members E, G, J and L simultaneously represent a carbon atom and when the $R_9$ radical is carried by the nitrogen atom of the unsaturated ring; or alternatively
2) when at least one of the ring members E, G, J and L represents a nitrogen atom to which the Rs radical is attached;
in the unsaturated cationic groups of formula (III):
when a=0, the linker arm D is attached to the nitrogen atom,
when a=1, the linker arm D is attached to one of the ring members E, G, J, L or M,
y can take the value 1 only when at least one of the ring members E, G, J, L and M represents a divalent atom and when the $R_9$ radical is carried by the nitrogen atom of the unsaturated ring;
in the cationic groups of formula (IV):
when a=0, then the linker arm D is attached to the nitrogen atom carrying the $R_{10}$ to $R_{12}$ radicals,
when a=1, then two of the $R_{10}$ to $R_{12}$ radicals form, together with the nitrogen atom to which they are attached, a saturated 5- or 6-membered ring as defined above, and the linker arm D is carried by a carbon atom of the saturated ring;
$X^-$ is a monovalent or divalent anion; with the proviso that the number of cationic Z groups in the compound of formula (I) is at least equal to 1.

11. The composition according to claim 10, wherein said at least one compound of formula (I) is present in said composition in an amount ranging from 0.0005 to 12% by weight relative to the total weight of the composition.

12. The composition according to claim 11, wherein said at least one compound of formula (I) is present in said composition in an amount ranging from 0.005 to 6% by weight relative to the total weight of the composition.

13. The composition according to claim 10, further comprising at least one oxidation base chosen from para-phenylenediamines, bis(phenyl)alkylenediamines, para-aminophenols, ortho-aminophenols and heterocyclic bases.

14. The composition according to claim 13, wherein the heterocyclic bases are chosen from pyridine derivatives, pyrimidine derivatives and pyrazole derivatives.

15. The composition according to claim 13, wherein said at least one oxidation base is present in said composition in an amount ranging from 0.0005 to 12% by weight relative to the total weight of the composition.

16. The composition according to claim 10, further comprising at least one coupler chosen from meta-phenylenediamines, meta-aminophenols, meta-diphenols and heterocyclic couplers, and/or at least one direct dye.

17. The composition according to claim 16, wherein said at least one coupler is chosen from 2-methyl-5-aminophenol, 5-N-(β-hydroxyethyl) amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy) benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one and 3,6-dimethylpyrazolo(3,2-c)-1,2, 4-triazole, and acid addition salts thereof.

18. The composition according to claim 16, wherein said at least one coupler is present in said composition in an amount ranging from 0.0001 to 10% by weight relative to the total weight of the composition.

19. The composition according to claim 10, wherein the acid addition salts are chosen from hydrochlorides, hydrobromides, sulphates, citrates, succinates, tartrates, lactates and acetates.

20. The composition according to claim 10, wherein said keratin fibers are human keratin fibers.

21. The composition according to claim 10, wherein said human keratin fibers are hair.

22. The composition according to claim 10, wherein in at least one of said formulae (II), (III), and (IV), D is a linear or branched alkyl chain containing from 1 to 14 carbon atoms.

23. The composition according to claim 10, wherein in at least one of said formulae (II), (III), and (IV), D can be interrupted by oxygen, sulphur, or nitrogen atoms.

24. A process for the oxidation-dyeing of keratin fibers comprising
applying to said keratin fibers for a period which is sufficient to develop the desired coloration, at least one dye composition comprising, in a medium suitable for dyeing, at least one compound of formula (I) below, or an acid addition salt thereof wherein said developing is carried out either in air or in the presence of an oxidizing agent:

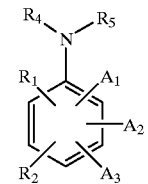

(I)

in which;
$A_1$, $A_2$ and $A_3$, which may be identical or different, are chosen from a group —$NR_7R_8$ and a hydroxyl radical; one and only one of the groups $A_1$, $A_2$ and $A_3$ may also represent a group $R_3$ as defined below;
$R_1$ $R_2$ and $R_3$, which may be identical or different, are chosen from a hydrogen atom; a halogen atom; a group Z as defined below; a ($C_1$–$C_6$)alkylcarbonyl radical; an amino($C_1$–$C_6$)alkylcarbonyl radical; an N—Z-amino ($C_1$–$C_6$)alkylcarbonyl radical; an N—($C_1$–$C_6$) alkylamino($C_1$–$C_6$)alkylcarbonyl radical; an N,N-di ($C_1$–$C_6$)-alkylamino($C_1$–$C_6$)alkylcarbonyl radical; an amino($C_1$–$C_6$)alkylcarbonyl($C_1$–$C_6$)alkyl radical; an N—Z-amino($C_1C_6$)alkylcarbonyl($C_1$–$C_6$)alkyl radical; an N—($C_1$–$C_6$)alkyl-amino($C_1$–$C_6$)alkylcarbonyl ($C_1$–$C_6$)alkyl radical; an N,N-di($C_1$–$C_6$)alkylamino ($C_1$–$C_6$)alkylcarbonyl($C_1$–$C_6$)alkyl radical; a carboxyl radical; a ($C_1$–$C_6$)alkylcarboxyl radical; a ($C_1$–$C_6$) alkylsulphonyl radical; an
aminosulphonyl radical; an N—Z-aminosulphonyl radical; a ($C_1$–$C_6$)N-alkylaminosulphonyl radical; an N,N-di($C_1$–$C_6$)alkylaminosulphonyl radical; a ($C_1$ –$C_6$) aminosulphonylalkyl radical; a ($C_1$–$C_6$)N—Z-aminosulphonylalkyl radical; an
N—($C_1$–$C_6$)alkylaminosulphonyl($C_1$–$C_6$)alkyl radical; an N,N-di($C_1$–$C_6$)-alkylaminosulphonyl($C_1$–$C_6$)alkyl radical; a carbamyl radical; an N—($C_1$–$C_6$) alkycarbamyl radical; an N,N-di($C_1$–$C_6$)alkylcarbamyl radical; a carbamyl($C_1$–$C_6$)alkyl radical; an N—($C_1$–$C_6$)alkylcarbamyl($C_1$–$C_6$)alkyl radical; an N,N-di($C_1$–$C_6$)alkylcarbamyl($C_1$–$C_6$)alkyl radical; a ($C_1$–$C_6$)alkyl radical: a ($C_1$–$C_6$)monohydroxyalkyl radical; a ($C_1$–$C_6$)polyhydroxyalkyl radical; a ($C_1$–$C_6$) alkoxy($C_1$–$C_6$)alkyl radical; a ($C_1$–$C_6$)trifluoroalkyl radical; a cyano radical; a group $OR_6$ or $SR_6$; an amino group protected by a $(C_1-C_6)$alkylcarbonyl, $(C_1-C_6)$alkylcarboxyl, trifluoro$(C_1-C_6)$alkylcarbonyl, amino$(C_1-C_6)$alkylcarbonyl, N—Z-amino$(C_1-C_6)$alkylcarbonyl, N—$(C_1-C_6)$alkylamino$(C_1-C_6)$alkylcarbonyl, N,N-di$(C_1-C_6)$alkylamino$(C_1-C_6)$alkylcarbonyl, $(C_1-C_6)$alkylcarboxyl, carbamyl, N—$(C_1-C_6)$alkylcarbamyl, N,N-di$(C_1-C_6)$alkylcarbamyl, $(C_1-C_6)$alkylsulphonyl, aminosulphonyl, N—Z-aminosulphonyl, $(C_1-C_6)$N-alkylaminosulphonyl, N,N-di$(C_1-C_6)$alkylaminosulphonyl, thiocarbamyl or formyl radical, or with a group Z as defined below in which a linker arm D comprises a ketone function directly attached to the nitrogen atom of the amino group; and a $(C_1-C_6)$aminoalkyl radical in which the alkyl is unsubstituted or substituted with one or more hydroxyl radicals; a $(C_1-C_6)$aminoalkyl radical in which the alkyl is unsubstituted or substituted with one or more hydroxyl radicals and in which the amine is substituted with one or two radicals, which may be identical or different, chosen from alkyl, $(C_1-C_6)$monohydroxyalkyl, $(C_1-C_6)$polyhydroxyalkyl, $(C_1-C_6)$alkylcarbonyl, carbamyl, N—$(C_1-C_6)$alkylcarbamyl, N,N-di$(C_1-C_6)$alkylcarbamyl, $C_1-C_6$ alkylsulphonyl, formyl, trifluoro$(C_1-C_6)$-alkylcarbonyl, $(C_1-C_6)$alkylcarboxyl and thiocarbamyl radicals, or from a group Z as defined below, or which may form, together with the nitrogen atom to which they are attached, a 5- or 6-membered ring which is carbon-based or which contains one or more hetero atoms;

$R_6$ is chosen from a $(C_1-C_6)$alkyl radical; a $(C_1-C_6)$monohydroxyalkyl radical; a $(C_2-C_6)$polyhydroxyalkyl radical; a group Z as defined below; a $(C_1-C_6)$alkoxy$(C_1-C_6)$alkyl radical; an aryl radical; a benzyl radical; a carboxy$(C_1-C_6)$alkyl radical; a $(C_1-C_6)$alkylcarboxy$(C_1-C_6)$alkyl radical; a cyano$(C_1-C_6)$alkyl radical; a carbamyl$(C_1-C_6)$alkyl radical; an N—$(C_1-C_6)$alkylcarbamyl$(C_1-C_6)$alkyl radical; an N,N-di$(C_1-C_6)$alkylcarbamyl$(C_1-C_6)$alkyl radical; a $(C_1-C_6)$trifluoroalkyl radical; a $(C_1-C_6)$aminosulphonylalkyl radical; a $(C_1-C_6)$N—Z-aminosulphonylalkyl radical; an N—$(C_1-C_6)$alkylaminosulphonyl$(C_1-C_6)$alkyl radical; an N,N-di$(C_1-C_6)$alkylaminosulphonyl$(C_1-C_6)$alkyl radical; a $(C_1-C_6)$alkylsulphinyl$(C_1-C_6)$alkyl radical; a $(C_1-C_6)$alkylsulphonyl $(C_1-C_6)$alkyl radical; a $(C_1-C_6)$alkylcarbonyl $(C_1-C_6)$alkyl radical; a $(C_1-C_6)$aminoalkyl radical in which the alkyl is unsubstituted or substituted with one or more hydroxyl radicals; and a $(C_1-C_6)$aminoalkyl radical in which the alkyl is unsubstituted or substituted with one or more hydroxyl radicals and in which the amine is substituted with one or two identical or different radicals chosen from $(C_1-C_6)$alkyl, $(C_1-C_6)$monohydroxyalkyl, $(C_2-C_6)$polyhydroxyalkyl, $(C_1-C_6)$alkylcarbonyl, formyl, trifluoro$(C_1-C_6)$alkylcarbonyl, $(C_1-C_6)$alkylcarboxyl, carbamyl, N—$(C_1-C_6)$alkylcarbamyl, N,N-di$(C_1-C_6)$alkylcarbamyl, thiocarbamyl and $(C_1-C_6)$alkylsulphonyl radicals, or from a group Z as defined below; or which may form, together with the nitrogen atom to which they are attached, a 5- or 6-membered ring which is carbon-based or which contains one or more hetero atoms;

$R_4$, $R_5$, $R_7$ and $R_8$, which may be identical or different, are chosen from a hydrogen atom; a group Z as defined below, in which the linker arm D contains no ketone functions directly linked to the nitrogen atom bearing the radicals $R_4$ and $R_5$; a $(C_1-C_6)$alkyl radical; a $(C_1-C_6)$monohydroxyalkyl radical; a $(C_2-C_6)$polyhydroxyalkyl radical, a $(C_1-C_6)$alkoxy$(C_1-C_6)$alkyl radical; an aryl radical; a benzyl radical; a cyano$(C_1-C_6)$alkyl radical; a carbamyl$(C_1-C_6)$alkyl radical; an N—$(C_1-C_6)$alkylcarbamyl$(C_1-C_6)$alkyl radical; an N,N-di$(C_1-C_6)$alkylcarbamyl$(C_1-C_6)$alkyl radical; a thiocarbamyl$(C_1-C_6)$alkyl radical; a $(C_1-C_6)$trifluoroalkyl radical; a $(C_1-C_6)$sulphoalkyl radical; a $(C_1-C_6)$alkylcarboxy$(C_1-C_6)$alkyl radical; a $(C_1-C_6)$alkylsulphinyl$(C_1-C_6)$alkyl radical; a $(C_1-C_6)$aminosulphonylalkyl radical; a $(C_1-C_6)$N—Z-aminosulphonylalkyl radical; an N—$(C_1-C_6)$alkylaminosulphonyl$(C_1-C_6)$alkyl radical; an N,N-di$(C_1-C_6)$alkylaminosulphonyl$(C_1-C_6)$alkyl radical; a $(C_1-C_6)$alkylcarbonyl$(C_1-C_6)$alkyl radical; a $(C_1-C_6)$aminoalkyl radical in which the alkyl is unsubstituted or substituted with one or more hydroxyl radicals; and a $(C_1-C_6)$aminoalkyl radical in which the alkyl is unsubstituted or substituted with one or more hydroxyl radicals and in which the amine is substituted with one or two identical or different radicals chosen from $(C_1-C_6)$alkyl, $(C_1-C_6)$monohydroxyalkyl, $(C_2-C_6)$polyhydroxyalkyl, $(C_1-C_6)$alkylcarbonyl, carbamyl, N—$(C_1-C_6)$alkylcarbamyl, N,N-di$(C_1-C_6)$alkylcarbamyl, $(C_1-C_6)$alkylsulphonyl, formyl, trifluoro$(C_1-C_6)$alkylcarbonyl, $(C_1-C_6)$alkylcarboxyl and thiocarbamyl radicals, or from a group Z as defined below; or which may form, together with the nitrogen atom to which they are attached, a 5- or 6-membered ring which is carbon-based or which contains one or more hetero atoms;

Z is chosen from the unsaturated cationic groups of formulae (II) and (III) below, and the saturated cationic groups of formula (IV) below:

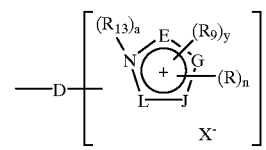

(II)

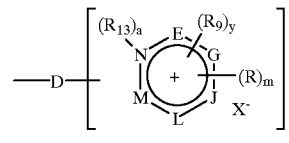

(III)

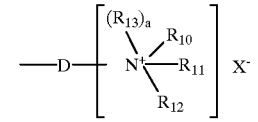

(IV)

in which:

D is a linker arm which represents a linear or branched alkyl chain, which can be interrupted by one or more hetero atoms, and which can be substituted with one or more hydroxyl or $C_1-C_6$ alkoxy radicals, and which can bear one or more ketone functions;

the ring members E, G, J, L and M, which may be identical or different, are chosen from a carbon, oxygen, sulphur and nitrogen;

n is an integer ranging from 0 to 4;

m is an integer ranging from 0 to 5;

the R radical, which may be identical or different, are chosen from a second Z group, which is identical to or different from the first Z group, a halogen atom, a hydroxyl radical, a $(C_1-C_6)$alkyl radical, a $(C_1-C_6)$ monohydroxyalkyl radical, a $(C_2-C_6)$ polyhydroxyalkyl radical, a nitro radical, a cyano radical, a cyano$(C_1-C_6)$alkyl radical, a $(C_1-C_6)$alkoxy radical, a tri$(C_1-C_6)$alkylsilane$(C_1-C_6)$alkyl radical, an amido radical, a formyl radical, a carboxyl radical, a $(C_1-C_6)$alkylcarbonyl radical, a thio radical, a $(C_1-C_6)$ thioalkyl radical, a $(C_1-C_6)$alkylthio radical, an amino radical, an amino radical protected with a $(C_1-C_6)$ alkylcarbonyl, carbamyl or $(C_1-C_6)$alkylsulphonyl radical; a group NHRO or NROR" in which RO and R", which may be identical or different, are chosen from a $(C_1-C_6)$alkyl radical, a $(C_1-C_6,)$monohydroxyalkyl radical and a $(C_2-C_6)$polyhydroxyalkyl radical;

$R_9$ is chosen from a $(C_1-C_6)$alkyl radical, a $(C_1-C_6)$ monohydroxyalkyl radical, a $(C_2-C_6)$ polyhydroxyalkyl radical, a cyano$(C_1-C_6)$alkyl radical, a tri$(C_1-C_6,)$alkylsilane$(C_1-C_6)$alkyl radical, a $(C_1-C_6)$ alkoxy$(C_1-C_6)$alkyl radical, a carbamyl-$(C_1-C_6)$alkyl radical, a $(C_1-C_6)$alkylcarboxy$(C_1-C_6)$-alkyl radical, a benzyl radical and a second Z group, which is identical to or different from the first Z group;

$R_{10}$ $R_{11}$ and $R_{12}$, which may be identical or different, are chosen from a $(C_1-C_6)$alkyl radical, a $(C_1-C_6)$ monohydroxyalkyl radical, a $(C_1-C_6)$ polyhydroxyalkyl radical, a $(C_1-C_6)$alkoxy$(C_1-C_6)$ alkyl radical, a cyano$(C_1-C_6)$alkyl radical, an aryl radical, a benzyl radical, a $(C_1-C_6)$amidoalkyl radical, a tri$(C_1-C_6)$alkylsilane$(C_1-C_6)$alkyl radical and a $(C_1-C_6)$aminoalkyl radical in which the amine is protected by a $(C_1-C_6)$alkylcarbonyl, carbamyl or $(C_1-C_6)$ alkylsulphonyl radical; two of the $R_{10}$, $R_{11}$, and $R_{12}$ radicals may also together form, with the nitrogen atom to which they are attached, a carbonaceous saturated 5- or 6-membered ring or which contains one or more hetero atoms, wherein said ring may be unsubstituted or substituted with a halogen atom, a hydroxyl radical, a $(C_1-C_6)$alkyl radical, a $(C_1-C_6)$monohydroxyalkyl radical, a $(C_2-C_6)$polyhydroxyalkyl radical, a nitro radical, a cyano radical, a cyano$(C_1-C_6)$alkyl radical, a $(C_1-C_6)$alkoxy radical, a tri$(C_1-C_6)$alkylsilane$(C_1-C_6)$ alkyl radical, an amido radical, a formyl radical, a carboxyl radical, a keto$(C_1-C_6)$alkyl radical, a thio radical, a $(C_1-C_6)$thioalkyl radical, a $(C_1-C_6)$alkylthio radical, an amino radical or an amino radical protected with a $(C_1-C_6)$alkylcarbonyl, carbamyl or $(C_1-C_6)$ alkylsulphonyl radical; one of the $R_{10}$, $R_{11}$, and $R_{12}$ radicals may also be chosen from a second Z group which is identical to or different from the first Z group;

$R_{13}$ is chosen from a $(C_1-C_6)$alkyl radical; a $(C_1-C_6)$ monohydroxy-alkyl radical; a $(C_2-C_6)$ polyhydroxyalkyl radical; an aryl radical; a benzyl radical; a $(C_1-C_6)$aminoalkyl radical, a $(C_1-C_6)$ aminoalkyl radical in which the amine is protected by a $(C_1-C_6)$alkylcarbonyl, carbamyl or $(C_1-C_6)$ alkylsulphonyl radical; a carboxy$(C_1-C_6)$alkyl radical; a cyano$(C_1-C_6)$alkyl radical; a carbamyl$(C_1-C_6)$alkyl radical; a $(C_1-C_6)$trifluoroalkyl radical; a tri$(C_1-C_6)$ alkylsilane$(C_1-C_6)$alkyl radical; a $(C_1-C_6)$ sulphonamidoalkyl radical; a $(C_1-C_6)$alkylcarboxy $(C_1-C_6)$alkyl radical; a $(C_1-C_6)$alkylsulphinyl$(C_1-C_6)$ alkyl radical; a $(C_1-C_6)$alkylsulphonyl$(C_1-C_6)$alkyl radical; a $(C_1-C_6)$alkylketo$(C_1-C_6)$alkyl radical; an N—$(C_1-C_6)$alkylcarbamyl$(C_1-C_6)$alkyl radical; and an N—$(C_1-C_6)$alkylsulphonamido$(C_1-C_6)$alkyl radical;

a and y are integers equal to 0 or 1; with the following conditions:

in the unsaturated cationic groups of formula (II):
when a=0, the linker arm D is attached to the nitrogen atom,
when a=1, the linker arm D is attached to one of the ring members E, G, J or L,
y can take the value 1 only:
1) when the ring members E, G, J and L simultaneously represent a carbon atom and when the $R_9$ radical is carried by the nitrogen atom of the unsaturated ring; or alternatively
2) when at least one of the ring members E, G, J and L represents a nitrogen atom to which the $R_9$ radical is attached;

in the unsaturated cationic groups of formula (III):
when a=0, the linker arm D is attached to the nitrogen atom,
when a=1, the linker arm D is attached to one of the ring members E, G, J, L or M,
y can take the value 1 only when at least one of the ring members E, G, J, L and M represents a divalent atom and when the $R_9$ radical is carried by the nitrogen atom of the unsaturated ring;

in the cationic groups of formula (IV):
when a=0, then the linker arm D is attached to the nitrogen atom carrying the $R_{10}$ to $R_{12}$ radicals,
when a=1, then two of the $R_{10}$ to $R_{12}$ radicals form, together with the nitrogen atom to which they are attached, a saturated 5- or 6-membered ring as defined above, and the linker arm D is carried by a carbon atom of the saturated ring;

X⁻ is a monovalent or divalent anion; with the proviso that the number of cationic Z groups in the compound of formula (I) is at least equal to 1.

25. The process according to claim 24, wherein in at least one of said formulae (II), (III), and (IV), D is a linear or branched alkyl chain containing from 1 to 14 carbon atoms.

26. The process according to claim 24, wherein in at least one of said formulae (II), (III), and (IV), D can be interrupted by oxygen, sulphur, or nitrogen atoms.

27. The process according to claim 24, wherein the coloration of the fibers can be carried out without the addition of an oxidizing agent, merely on contact with atmospheric oxygen.

28. The process according to claim 24, wherein color is developed at acidic, neutral or alkaline pH using an oxidizing agent which is added to the dye composition at the time of application, or which is present in an oxidizing composition that is applied simultaneously or sequentially in a separate manner.

29. The process according to claim 24, wherein the oxidizing agent is chosen from hydrogen peroxide, urea peroxide, alkali metal bromates, persalts and enzymes.

30. The process according to claim 29, wherein the enzymes are chosen from peroxidases, laccases, tyrosinases and oxidoreductases.

31. The process according to claim 30, wherein the oxidoreductases are chosen from pyranose oxidases, glucose oxidases, glycerol oxidases, lactate oxidases, pyruvate oxidases and uricases.

32. The process according to claim 24, wherein the keratin fibers are human keratin fibers.

33. The process according to claim 24, wherein the human keratin fibers are hair.

34. A multi-compartment dyeing device comprising a first compartment and a second compartment, wherein said first compartment contains a dye composition comprising at least one dye composition comprising at least one compound of formula (I) below, or an acid addition salt thereof:

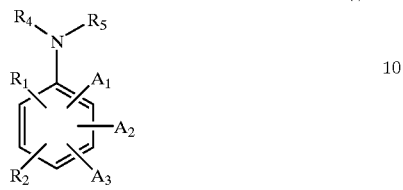

in which:

$A_1$, $A_2$ and $A_3$, which may he identical or different, are chosen from a group —$NR_7R_8$ and a hydroxyl radical; one and only one of the groups $A_1$, $A_2$ and $A_3$ may also represent a group $R_3$ as defined below;

$R_1$, $R_2$ and $R_3$, which may be identical or different, are chosen from a hydrogen atom; a halogen atom; a group Z as defined below; a $(C_1-C_6)$alkylcarbonyl radical; an amino$(C_1-C_6)$alkylcarbonyl radical; an N—Z-amino$(C_1-C)$alkylcarbonyl radical, an N—$(C_1-C_6)$ alkylamino$(C_1-C_6)$alkylcarbonyl radical; an N,N-di $(C_1-C_6)$-alkylamino$(C_1-C_6)$alkylcarbonyl radical; an amino$(C_1-C_6)$alkylcarbonyl$(C_1-C_6)$alkyl radical; an N—Z-amino$(C_1-C_6)$alkylcarbonyl$(C_1-C_6)$alkyl radical; an N$(C_1-C_6)$alkyl-amino$(C_1-C_6)$alkylcarbonyl $(C_1-C_6)$alkyl radical; an N,N-di$(C_1-C_6)$alkylamino $(C_1-C_6)$alkylcarbonyl$(C_1-C_6)$alkyl radical; a carboxyl radical; a $(C_1-C_6)$alkylcarboxyl radical; a $(C_1-C_6)$ alkylsulphonyl radical; an aminosulphonyl radical; an N—Z-aminosulphonyl radical; a $(C_1-C_6)$N-alkylaminosulphonyl radical; an N,N-di$(C_1-C_6)$ alkylaminosulphonyl radical; a $(C_1-C_6)$ aminosulphonylalkyl radical; a $(C_1-C_6)$N—Z-aminosulphonylalkyl radical; an N—$(C_1-C_6)$ alkylaminosulphonyl$(C_1-C_6)$alkyl radical; an N,N-di $(C_1-C_6)$-alkylaminosulphonyl$(C_1-C_6)$alkyl radical; a carbamyl radical; an N—$(C_1-C_6)$alkylcarbamyl radical; an N,N-di$(C_1-C_6)$alkylcarbamyl radical; a carbamyl$(C_1-C_6)$alkyl radical; an N—$(C_1-C_6)$ alkylcarbamyl$(C_1-C_6)$alkyl radical; an N,N-di$(C_1-C_6)$ alkylcarbamyl$(C_1-C_6)$alkyl radical; a $(C_1-C_6)$alkyl radical; a $(C_1-C_6)$monohydroxyalkyl radical; a $(C_2-C_6)$polyhydroxyalkyl radical; a $(C_1-C_6)$alkoxy $(C_1-C_6)$alkyl radical; a $(C_1-C_6)$trifluoroalkyl radical; a cyano radical; a group $OR_6$ or $SR_6$; an amino group protected by a $(C_1-C_6)$alkylcarbonyl, $(C_1-C_6)$ alkylcarboxyl, trifluoro$(C_1-C_6)$alkylcarbonyl, amino $(C_1-C_6)$alkylcarbonyl, N—Z-amino$(C_1-C_6)$ alkylcarbonyl, N-$(C_1-C_6)$alkylamino$(C_1-C_6)$ alkylcarbonyl, N,N-di$(C_1-C_6)$alkylamino$(C_1-C_6)$ alkylcarbonyl, $(C_1-C_6)$alkylcarboxyl, carbamyl, N—$(C_1-C_6)$alkylcarbamyl, N,N-di$(C_1-C_6)$ alkylcarbamyl, $(C_1-C_6)$alkylsulphonyl, aminosulphonyl, N—Z-aminosulphonyl, $(C_1-C_6)$N-alkylaminosulphonyl, N,N-di$(C_1-C_6)$ alkylaminosulphonyl, thiocarbamyl or formyl radical, or with a group Z as defined below in which a linker arm D comprises a ketone function directly attached to the nitrogen atom of the amino group; and a $(C_1-C_6)$ aminoalkyl radical in which the alkyl is unsubstituted or substituted with one or more hydroxyl radicals; a $(C_1-C_6)$aminoalkyl radical in which the alkyl is unsubstituted or substituted with one or more hydroxyl radicals and in which the amine is substituted with one or two radicals, which may be identical or different, chosen from alkyl, $(C_1-C_6)$monohydroxyalkyl, $(C_2-C_6)$polyhydroxyalkyl, $(C_1-C_6)$alkylcarbonyl, carbamyl, N—$(C_1-C_6)$alkylcarbamyl, N,N-di$(C_1l_6)$ alkylcarbamyl, $C_1-C_6$ alkylsulphonyl, formyl, trifluoro $(C_1-C_6)$-alkylcarbonyl, $(C_1-C_6)$alkylcarboxyl and thiocarbamyl radicals, or from a group Z as defined below, or which may form, together with the nitrogen atom to which they are attached, a 5- or 6-membered ring which is carbon-based or which contains one or more hetero atoms;

$R_6$ is chosen from a $(C_1-C_6)$alkyl radical; a $(C_1-C_6)$ monohydroxyalkyl radical; a $(C_2C_6)$polyhydroxyalkyl radical; a group Z as defined below; a $(C_1-C_6)$alkoxy $(C_1-C_6)$alkyl radical; an aryl radical; a benzyl radical; a carboxy$(C_1-C_6)$alkyl radical; a $(C_1-C_6)$alkylcarboxy $(C_1-C_6)$alkyl radical; a cyano$(C_1-C_6)$alkyl radical; a carbamyl$(C_1-C_6)$alkyl radical; an N—$(C_1-C_6)$ alkylcarbamyl$(C_1-C_6)$alkyl radical; an N,N-di$(C_1-C_6)$ alkylcarbamyl$(C_1-C_6)$alkyl radical; a $(C_1-C_6)$ trifluoroalkyl radical; a $(C_1-C_6)$aminosulphonylalkyl radical; a $(C_1-C_6)$N—Z-aminosulphonylalkyl radical; an N—$(C_1-C_6)$alkylaminosulphonyl$(C_1-C_6)$alkyl radical; an N,N-di$(C_1-C_6)$alkylaminosulphonyl$(C_1-C_6)$ alkyl radical; a $(C_1-C_6)$alkylsulphinyl $(C_1-C_6$ alkyl radical; a $(C_1-C_6)$alkylsulphonyl $(C_1-C_6)$alkyl radical; a $(C_1-C_6)$alkylcarbonyl $(C_1-C_6)$alkyl radical; a $(C_1-C_6)$aminoalkyl radical in which the alkyl is unsubstituted or substituted with one or more hydroxyl radicals; and a $(C_1-C_6)$aminoalkyl radical in which the alkyl is unsubstituted or substituted with one or more hydroxyl radicals and in which the amine is substituted with one or two identical or different radicals chosen from $(C_1-C_6)$alkyl, $(C_1-C_6)$monohydroxyalkyl, $(C_2-C_6)$polyhydroxyalkyl, $(C_1-C_6)$alkylcarbonyl, formyl, trifluoro$(C_1-C_6)$alkylcarbonyl, $(C_1-C_6)$ alkylcarboxyl, carbamyl, N—$(C_1-C_6)$alkylcarbamyl, N,N-di$(C_1-C_6)$alkylcarbamyl, thiocarbamyl and $(C_1-C_6)$alkylsulphonyl radicals, or from a group Z as defined below; or which may form, together with the nitrogen atom to which they are attached, a 5- or 6-membered ring which is carbon-based or which contains one or more hetero $R_4$, $R_5$, $R_7$ and $R_8$, which may be identical or different are chosen from a hydrogen atom; a group Z as defined below, in which the linker arm D contains no ketone functions directly linked to the nitrogen atom bearing the radicals $R_4$ and $R_5$; a $(C_1-C_6)$alkyl radical; a $(C_1-C_6)$monohydroxyalkyl radical; a $(C_2-C_6)$ polyhydroxyalkyl radical; a $(C_1Gr)$alkoxy$(C_1-C_6)$alkyl radical; an aryl radical; a benzyl radical; a cyano $(C_1-C_6)$alkyl radical; a carbamyl$(C_1-C_6)$alkyl radical; an N—$(C_1-C_6)$alkylcarbamyl$(C_1-C_6)$alkyl radical; an N,N-di$(C_1-C_6)$alkylcarbamyl$(C_1-C_6)$alkyl radical; a thiocarbamyl$(C_1-C_6)$alkyl radical; a $(C_1-C_6)$ trifluoroalkyl radical; a $(C_1-C_6)$sulphoalkyl radical; a $(C_1-C_6)$alkylcarboxy$(C_1-C_6)$alkyl radical: a $(C_1-C_6)$ alkylsulphinyl$(C_1-C_6)$alkyl radical; a $(C_1-C_6)$ aminosulphonylalkyl radical; a $(C_1-C_6)$N—Z-aminosulphonylalkyl radical; an N—$(C_1C_6)$ alkylaminosulphonyl$(C_1-C_6)$alkyl radical; an N,N-di $(C_1-C_6)$alkylaminosulphonyl$(C_1-C_6)$alkyl radical; a $(C_1-C)$alkylcarbonyl$(C_1-C_6)$alkyl radical; a $(C_1-C_6)$ aminoalkyl radical in which the alkyl is unsubstituted or substituted with one or more hydroxyl radicals; and a $(C_1-C_6)$aminoalkyl radical in which the alkyl is unsubstituted or substituted with one or more hydroxl radicals and in which the amine is substituted with one or two identical or different radicals chosen from $(C_1-C_6)$alkyl, $(C_1-C_6)$monohydroxyalkyl, $(C_2-C_6)$polyhydroxyalkyl, $(C_1-C_6)$alkylcarbonyl, carbamyl, N—$(C_1-C_6)$alkylcarbamyl, N,N-di$(C_1-C_6)$alkylcarbamyl, $(C_1-C_6)$alkylsulphonyl, formyl, trifluoro$(C_1-C_6)$alkylcarbonyl, $(C_1-C_6)$alkylcarboxyl and thiocarbamyl radicals, or from a group Z as defined below; or which may form, together with the nitrogen atom to which they are attached, a 5- or 6-membered ring which is carbon-based or which contains one or more hetero atoms;

Z is chosen from the unsaturated cationic groups of formulae (II) and (III) below, and the saturated cationic groups of formula (IV) below:

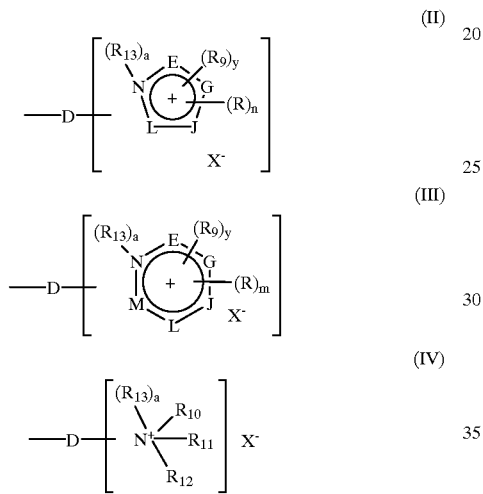

in which:
D is a linker arm which represents a linear or branched alkyl chain, which can be interrupted by one or more hetero atoms, and which can be substituted with one or more hydroxyl or $C_1-C_6$ alkoxy radicals, and which can bear one or more ketone functions; the ring members E, G, J, L and M, which may be identical or different, are chosen from a carbon, oxygen, sulphur and nitrogen;
n is an integer ranging from 0 to 4;
m is an integer ranging from 0 to 5;
the R radical, which may be identical or different are chosen from a second Z group, which is identical to or different from the first Z group, a halogen atom, a hydroxyl radical, a $(C_1-C_6)$alkyl radical, a $(C_1-C_6)$monohydroxyalkyl, radical, a $(C_2-C_6)$polyhydroxyalkyl radical, a nitro radical, a cyano radical, a cyano$(C_1-C_6)$alkyl radical, a $(C_1-C_6)$alkoxy radical, a tri$(C_1-C_6)$alkylsilane$(C_1-C_6)$alkyl radical, an amido radical, a formyl radical, a carboxyl radical, a $(C_1-C_6)$alkylcarbonyl radical, a thic) radical, a $(C_1-C_6)$thioalkyl radical, a $(C_1-C_6)$alkylthio radical, an amino radical, an amino radical protected with a $(C_1-C_6)$alkylcarbonyl, carbamyl or $(C_1-C_6)$alkylsulphonyl radical; a group NHRO or NROR" in which RO and R", which may be identical or different, are chosen from a $(C_1-C_6)$alkyl radical, a $(C_1-C_6)$monohydroxyalkyl radical and a $(C_2-C_6)$polyhydroxyalkyl radical;

$R_9$ is chosen from a $(C_1-C_6)$alkyl radical, a $(C_1-C_6)$monohydroxyalkyl radical, a $(C_2-C_6)$polyhydroxyalkyl radical, a cyano$(C_1-C_6)$alkyl radical, a tri$(C_1-C_6)$alkylsilane$(C_1-C_6)$alkyl radical, a $(C_1-C_6)$alkoxy$(C_1-C_6)$alkyl radical, a carbamyl-$(C_1-C_6)$alkyl radical, a $(C_1-C_6)$alkylcarboxy$(C_1-C_6)$-alkyl radical, a benzyl radical and a second Z group, which is identical to or different from the first Z group;

$R_{10}$, $R_{11}$ and $R_{12}$, which may be identical or different, are chosen from a $(C_1-C_6)$alkyl radical, a $(C_1-C_6)$monohydroxyalkyl radical, a $(C_2-C_6)$polyhydroxyalkyl radical, a $(C_1-C_6)$alkoxy$(C_1-C_6)$alkyl radical, a cyano$(C_1-C_6)$alkyl radical, an aryl radical, a benzyl radical, a $(C_1-C_6)$amidoalkyl radical, a tri$(C_1-C_6)$alkylsilane$(C_1-C_6)$alkyl radical and a $(C_1-C_6)$aminoalkyl radical in which the amine is protected by a $(C_1-C_6)$alkylcarbonyl, carbamyl or $(C_1-C_6)$alkylsulphonyl radical; tho of the $R_{10}$, $R_{11}$ and $R_{12}$ radicals may also together form, with the nitrogen atom to which they are attached, a carbonaceous saturated 5- or 6remembered ring or which contains one or more hetero atoms, wherein said ring may be unsubstituted or substituted with a halogen atom, a hydroxyl radical, a $(C_1-C_6)$alkyl radical, a $(C_1-C_6)$monohydroxyalkyl radical, a $(C_2-C_6)$polyhydroxyalkyl radical, a nitro radical, a cyano radical, a cyano$(C_1-C_6)$alkyl radical, a $(C_1-C_6)$alkoxy radical, a tri$(C_1-C_6)$alkylsilane$(C_1-C_6)$ alkyl radical, an amido radical, a formyl radical, a carboxyl radical, a keto$(C_1-C_6)$alkyl radical, a thio radical, a $(C_1-C_6)$thioalkyl radical, a $(C_1-C_6)$alkylthio radical, an amino radical or an amino radical protected with a $(C_1-C_6)$alkylcarbonyl, carbamyl or $(C_1-C_6)$alkylsulphonyl radical; one of the $R_{10}$, $R_{11}$ and $R_{12}$ radicals may also be chosen from a second Z group which is identical to or different from the first Z group;

$R_{13}$ is chosen from a $(C_1-C_6)$alkyl radical; a $(C_1-C_6)$monohydroxy-alkyl radical; a $(C_2-C_6)$polyhydroxyalkyl radical; an aryl radical; a benzyl radical; a $(C_1-C_6)$aminoalkyl radical, a $(C_1-C_6)$aminoalkyl radical in which the amine is protected by a $(C_1-C_6)$alkylcarbonyl, carbamyl or $(C_1-C_6)$alkylsulphonyl radical; a carboxy$(C_1-C_6)$alkyl radical; a cyano$(C_1-C_6)$alkyl radical; a carbamyl$(C_1-C_6)$alkyl radical; a $(C_1-C_6)$trifluoroalkyl radical; a tri$(C_1-C_6)$alkylsilane$(C_1-C_6)$alkyl radical; a $(C_1-C_6)$sulphonamidoalkyl radical; a $(C_1-C_6)$alkylcarboxy$(C_1-C_6)$alkyl radical; a $(C_1-C_6)$alkylsulphinyl$(C_1-C_6)$alkyl radical; a $(C_1-C_6)$alkylsulphonyl$(C_1-C_6)$alkyl radical; a $(C_1-C_6)$alkylketo$(C_1-C_6)$alkyl radical; an N—$(C_1-C_1)$alkylcarbamyl$(C_1-C_6)$alkyl radical; and an N—$(C_1-C_6)$alkylsulphonamido$(C_1-C_6)$alkyl radical;

a and y are integers equal to 0 or 1; with the following conditions: in the unsaturated cationic groups of formula (II):
when a=0, the linker arm D is attached to the nitrogen atom,
when a=1, the linker arm D is attached to one of the ring members E, G, J or L vertices,
y can take the value 1 only:
1) when the ring members E, G, J and L simultaneously represent a carbon atom and when the $R_9$ radical is carried by the nitrogen atom of the unsaturated ring; or alternatively 2) when at least one of the ring members E, G, J and L represents a nitrogen atom to which the $R_9$ radical is attached;

in the unsaturated cationic groups of formula (III):

when a=0, the linker arm D is attached to the nitrogen atom, when a=1, the linker arm D is attached to one of the ring members E, G, J, L or M, y can take the value 1 only when at least one of the ring members E, G, J, L and M represents a divalent atom and when the $R_9$ radical is carried by the nitrogen atom of the unsaturated ring;

in the Qationic groups of formula (IV):

when a=0, then the linker arm D is attached to the nitrogen atom carrying the $R_{10}$ to $R_{12}$ radicals, when a=1, then two of the $R_{10}$ to $R_{12}$ radicals form, together with the nitrogen atom to which they are attached, a saturated 5- or 6-membered ring as defined above, and the linker arm D is carried by a carbon atom of the saturated ring;

$X^-$ is a monovalent or divalent anion;

with the proviso that the number of cationic Z groups in the compound of formula (I) is at least equal to 1; and wherein said second compartment contains an oxidizing composition.

35. The multi-compartment dyeing device according to claim 34, wherein in at least one of said formulae (II), (III), and (IV), D is a linear or branched alkyl chain containing from 1 to 14 carbon atoms.

36. The multi-compartment dyeing device according to claim 34, wherein in at least one of said formulae (II), (III), and (IV), D can be interrupted by oxygen, sulphur, or nitrogen atoms.

* * * * *

UNITED STATES PATENT AND TRADEMARK OFFICE
CERTIFICATE OF CORRECTION

PATENT NO. : 6,383,230 B1
DATED : May 7, 2002
INVENTOR(S) : Genet et al.

It is certified that error appears in the above-identified patent and that said Letters Patent is hereby corrected as shown below:

Title page,
Item [73] insert "S.A.." after -- L'Oreal --.
Item [75] "Alan Lagrange" should read -- Alain Lagrange --.

Column 18,
Line 57, "cartamyl" should read -- carbamyl --.
Line 60, "thiocatamyl" should read -- thiocarbamyl --.

Column 19,
Line 32, "Identical" should read -- identical --.

Column 21,
Line 32, "alkyolsilane" should read -- alkylsilane --.
Line 42, "a 0" should read -- a=0 --.

Column 22,
Line 53, "3-methyl-3H-imidazo 1-ium" should read -- 3-methyl-3H-imidazol 1-ium --.

Column 27,
Line 4, "$R_S$" should read -- $R_9$ --.

Column 29,
Line 23, "$C_1$-$C_6$ polyhydroxyalkyl" should read -- $C_2$-$C_6$ polyhydroxyalkyl --.

Column 30,
Line 4, "$C,1$-$C_6$" alkyl radical" should read -- $C_1$-$C_6$ --.

Column 31,
Line 30, "$C_1$-$C_6$ polyhydroxyalkyl" should read -- $C_2$-$C_6$ polyhydroxyalkyl --.

Column 33,
Line 26, "($C_1$-C)alkycarbonyl" should read -- ($C_1$-$C_6$)alkycarbonyl --.

Column 34,
Line 7, "N,N-di($C_1 1_6$)" should read -- N,N-di($C_1$-$C_6$) --.
Line 53, "($C_1$Gr)alkoxy" should read -- ($C_1$-$C_6$)alkoxy --.

UNITED STATES PATENT AND TRADEMARK OFFICE
CERTIFICATE OF CORRECTION

PATENT NO.   : 6,383,230 B1
DATED        : May 7, 2002
INVENTOR(S)  : Genet et al.

It is certified that error appears in the above-identified patent and that said Letters Patent is hereby corrected as shown below:

Column 35,
Line 3, "hydroxl" should read -- hydroxyl --.
Line 60, "a thic) radical" should read -- a thio radical --.

Column 36,
Line 18, "tho" should read -- two --.
Line 21, "6remembered" should read -- 6-membered --.
Line 54, "N-$(C_1-C_1)$" should read -- N-$(C_1-C_6)$ --.

Column 37,
Line 13, "Qationic" should read -- cationic --.

Signed and Sealed this

Thirtieth Day of July, 2002

Attest:

JAMES E. ROGAN
*Attesting Officer*    *Director of the United States Patent and Trademark Office*